US008623366B2

(12) United States Patent
Pios et al.

(10) Patent No.: US 8,623,366 B2
(45) Date of Patent: Jan. 7, 2014

(54) METHODS FOR TREATING VISCERAL PAIN BY ADMINISTERING ANTAGONIST ANTIBODIES DIRECTED AGAINST CALCITONIN GENE-RELATED PEPTIDE

(75) Inventors: Ariel Ates Pios, Pacifica, CA (US); Kristian Todd Poulsen, San Francisco, CA (US); David Louis Shelton, Oakland, CA (US); Joerg Zeller, Ann Arbor, MI (US)

(73) Assignee: Labrys Biologics, Inc., San Mateo, CA (US)

( * ) Notice: Subject to any disclaimer, the term of this patent is extended or adjusted under 35 U.S.C. 154(b) by 0 days.

(21) Appl. No.: 13/392,860

(22) PCT Filed: Aug. 23, 2010

(86) PCT No.: PCT/IB2010/053787
§ 371 (c)(1),
(2), (4) Date: Feb. 27, 2012

(87) PCT Pub. No.: WO2011/024113
PCT Pub. Date: Mar. 3, 2011

(65) Prior Publication Data
US 2012/0225075 A1    Sep. 6, 2012

Related U.S. Application Data

(60) Provisional application No. 61/237,901, filed on Aug. 28, 2009.

(51) Int. Cl.
*A61K 39/395*    (2006.01)
*C12P 21/06*    (2006.01)
*C07K 16/00*    (2006.01)

(52) U.S. Cl.
USPC ............... 424/145.1; 424/130.1; 424/133.1; 424/141.1; 530/387.7; 530/387.3; 530/388.1; 530/388.24

(58) Field of Classification Search
None
See application file for complete search history.

(56) References Cited

U.S. PATENT DOCUMENTS

| 5,116,964 | A | 5/1992 | Capon et al. |
| 7,479,488 | B2 | 1/2009 | Mueller et al. |
| 8,007,794 | B2 | 8/2011 | Zeller et al. |
| 2004/0110170 | A1 | 6/2004 | Pisegna et al. |
| 2005/0234054 | A1 | 10/2005 | Mueller et al. |
| 2006/0183700 | A1 | 8/2006 | Vater et al. |
| 2011/0054150 | A1 | 3/2011 | Poulsen et al. |
| 2011/0257371 | A1 | 10/2011 | Poulsen et al. |
| 2012/0009192 | A1 | 1/2012 | Zeller et al. |

FOREIGN PATENT DOCUMENTS

| EP | 0212432 A1 | 3/1987 |
| EP | 1 031 350 A1 | 8/2000 |
| JP | 08-268874 A | 10/1996 |
| RU | 2329062 C2 | 7/2008 |
| WO | WO 2005/009962 A1 | 2/1955 |
| WO | WO 03/093472 A2 | 11/2003 |
| WO | WO 2004/003019 A2 | 1/2004 |
| WO | WO 2003/093472 A3 | 3/2004 |
| WO | WO 2004/003019 A3 | 9/2004 |
| WO | WO 2005/100360 A1 | 10/2005 |
| WO | WO 2006/077212 A1 | 7/2006 |
| WO | WO 2007/025212 A2 | 3/2007 |
| WO | WO 2007/054800 A2 | 5/2007 |
| WO | WO 2007/054809 A2 | 5/2007 |
| WO | WO 2007/061676 A2 | 5/2007 |
| WO | WO 2007/076336 A1 | 7/2007 |
| WO | WO 2007/054809 A3 | 8/2007 |
| WO | WO 2007/061676 A3 | 12/2007 |
| WO | WO 2008/011190 A1 | 1/2008 |

OTHER PUBLICATIONS

Adwanikar, H. et al., "Spinal CGRP1 receptors contribute to supraspinally organized pain behavior and pain-related sensitization of amygdala neurons," *Pain*, 2007, 53-66, vol. 132, No. 1-2.
Aziz, Q., "Visceral Hypersensitivity: Fact or Fiction," *Gastroenterology*, 2006, 661-664, vol. 131, No. 2.
Bennett, A., et al., "Alleviation of Mechanical and Thermal Allodynia by $CGRP8_{8-37}$ in a Rodent Model of Chronic Central Pain," *Pain*, 2000, 163-175, vol. 86, No. 1-2.
Delafoy, L., et al., "Interactive Involvement of Brain Derived Neurotrophic Factor, Nerve Growth Factor, and Calcitonin Gene Related Peptide in Colonic Hypersensitivity in the Rat," *Gut*, 2006, 940-945, vol. 55, No. 7.
International Search Report mailed Nov. 11, 2010 for PCT Application No. PCT/IB2010/053787 filed Aug. 23, 2010, nine pages.
Julia, V., et al., "Tachykininergic Mediation of Viscerosensitive Responses to Acute Inflammation in Rats: Role of CGRP," *The American Journal of Physiology*, 1997, G141-G146, vol. 272, No. 1.
Kawamura, M., et al., "Antinociceptive Effect of Intrathecally Administered Antiserum against Calcitonin Gene-Related Peptide on Thermal and Mechanical Noxious Stimuli in Experimental Hyperalgesic Rats," *Brain Research*, 1989, 199-203, vol. 497, No. 1.
Kuraishi, Y., et al., "Antinociception Induced in Rats by Intrathecal Administration of Antiserum against Calcitonin Gene-Related Peptide," *Neuroscience Letters*, 1988, 325-329, vol. 92, No. 3.
Wong, H., et al., "Monoclonal Antibody to Rat α-CGRP: Production, Characterization, and In Vivo Immunoneutralization Activity," *Hybridoma*, 1993, 93-106, vol. 12, No. 1.
Written Opinion issued on Nov. 11, 2010 for International Appln. No. PCT/IB2010/053787.
Zeller, J., et al., "CGRP Function-Blocking Antibodies Inhibit Neurogenic Vasodilatation without Affecting Heart Rate or Arterial Blood Pressure in the Rat," *British Journal of Pharmacology*, 2008, 1093-1103, vol. 155, No. 7.
U.S. Appl. No. 13/621,981, filed Sep. 18, 2012, Poulsen et al.
U.S. Appl. No. 13/623,206, filed Sep. 20, 2012, Poulsen et al.

(Continued)

*Primary Examiner* — Christine J Saoud
*Assistant Examiner* — Jon M Lockard
(74) *Attorney, Agent, or Firm* — Wilson Sonsini Goodrich & Rosati

(57) ABSTRACT

The invention features methods for preventing or treating visceral pain, including pain associated with functional bowel disorder, inflammatory bowel disease and interstitial cystitis, by administering an anti-CGRP antagonist antibody.

19 Claims, 2 Drawing Sheets

(56) References Cited

OTHER PUBLICATIONS

Ambalavanar, et al. Deep tissue inflammation upregulates neuropeptides and evokes nociceptive behaviors which are modulated by a neuropeptide antagonist. Pain. Jan. 2006;120(1-2):53-68. Epub Dec. 13, 2005.
ATCC website search for PTA-6866 deposit (p. 1; Oct. 22, 2010).
ATCC website search for PTA-6867 deposit (p. 1; Oct. 22, 2010).
Balint, et al. Antibody engineering by parsimonious mutagenesis. Gene. Dec. 27, 1993;137(1):109-18.
Brorson, et al. Mutational analysis of avidity and fine specificity of anti-levan antibodies. J Immunol. Dec. 15, 1999;163(12):6694-701.
Brummell, et al. Probing the combining site of an anti-carbohydrate antibody by saturation-mutagenesis: role of the heavy-chain CDR3 residues. Biochemistry. Feb. 2, 1993;32(4):1180-7.
Buckley, et al. The partial inhibition of inflammatory responses induced by capsaicin using the Fab fragment of a selective calcitonin gene-related peptide antiserum in rabbit skin. Neuroscience. Jun. 1992;48(4):963-8.
Burks, et al. In vitro scanning saturation mutagenesis of an antibody binding pocket. Proc Natl Acad Sci U S A. Jan. 21, 1997;94(2):412-7.
Casset, et al. A peptide mimetic of an anti-CD4 monoclonal antibody by rational design. Biochem Biophys Res Commun. Jul. 18, 2003;307(1):198-205.
Chen, et al. Selection and analysis of an optimized anti-VEGF antibody: crystal structure of an affinity-matured Fab in complex with antigen. J Mol Biol. Nov. 5, 1999;293(4):865-81.
Colman. Effects of amino acid sequence changes on antibody-antigen interactions. Res Immunol. Jan. 1994;145(1):33-6.
Davies, et al. Affinity improvement of single antibody VH domains: residues in all three hypervariable regions affect antigen binding. Immunotechnology. Sep. 1996;2(3):169-79.
De Pascalis, et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Dufner, et al. Harnessing phage and ribosome display for antibody optimisation. Trends Biotechnol. Nov. 2006;24(11):523-9. Epub Sep. 26, 2006.
Elshourbagy, et al. Molecular cloning and characterization of the porcine calcitonin gene-related peptide receptor. Endocrinology. Apr. 1998;139(4):1678-83.
European search report dated May 8, 2012 for EP Application No. 11166787.9.
Frobert, et al. A sensitive sandwich enzyme immunoassay for calcitonin gene-related peptide (CGRP): characterization and application. Peptides. 1999;20(2):275-84.
Holm, et al. Functional mapping and single chain construction of the anti-cytokeratin 8 monoclonal antibody TS1. Mol Immunol. Feb. 2007;44(6):1075-84. Epub Sep. 20, 2006.
Holt, et al. Domain antibodies: proteins for therapy. Trends Biotechnol. Nov. 2003;21(11):484-90.
International seach report and written opinion dated May 9, 2007 for PCT/IB2006/003181.
International seach report and written opinion dated Jul. 29, 2009 for PCT/IB2009/050852.
International seach report and written opinion dated Jul. 31, 2009 for PCT/IB2009/050849.
Jang, et al. The structural basis for DNA binding by an anti-DNA autoantibody. Mol Immunol. Dec. 1998;35(18):1207-17.
Kobayashi, et al. Tryptophan H33 plays an important role in pyrimidine (6-4) pyrimidone photoproduct binding by a high-affinity antibody. Protein Eng. Oct. 1999;12(10):879-84.
Kumar, et al. Molecular cloning and expression of the Fabs of human autoantibodies in Escherichia coli. Determination of the heavy or light chain contribution to the anti-DNA/-cardiolipin activity of the Fab. J Biol Chem. Nov. 10, 2000;275(45):35129-36.
Little, et al. Of mice and men: hybridoma and recombinant antibodies. Immunol Today. Aug. 2000;21(8):364-70.
MacCallum, et al. Antibody-antigen interactions: contact analysis and binding site topography. J Mol Biol. Oct. 11, 1996;262(5):732-45.
Mullins, et al. Characterization of a calcitonin gene-related peptide (CGRP) receptor on mouse bone marrow cells. Regul Pept. Nov. 19, 1993;49(1):65-72. (Abstract only).
Office action dated Mar. 1, 2012 for U.S. Appl. No. 12/920,621.
Office action dated Oct. 29, 2010 for U.S. Appl. No. 12/093,638.
Office action dated Dec. 20, 2011 for U.S. Appl. No. 12/920,634.
Plourde, et al. CGRP antagonists and capsaicin on celiac ganglia partly prevent postoperative gastric ileus. Peptides. Nov.-Dec. 1993;14(6):1225-9.
Rovero, et al. CGRP Antagonist Activity of Short C-Terminal Fragments of Human aCGRP, CGRP(23-37) and CGRP(19-37), Peptides, 1992, 1025-1027, vol. 13.
Rudikoff, et al. Single amino acid substitution altering antigen-binding specificity. Proc Natl Acad Sci U S A. Mar. 1982;79(6):1979-83.
Schaible, et al. Mechanisms of pain in arthritis. Ann N Y Acad Sci. Jun. 2002;966:343-54.
Smith-Gill, et al. Contributions of immunoglobulin heavy and light chains to antibody specificity for lysozyme and two haptens. J Immunol. Dec. 15, 1987;139(12):4135-44.
Song, et al. Light chain of natural antibody plays a dominant role in protein antigen binding. Biochem Biophys Res Commun. Feb. 16, 2000;268(2):390-4.
Tamura, et al. Structural correlates of an anticarcinoma antibody: identification of specificity-determining residues (SDRs) and development of a minimally immunogenic antibody variant by retention of SDRs only. J Immunol. Feb. 1, 2000;164(3):1432-41.
Tan, et al. Calcitonin gene-related peptides as an endogenous vasodilator:immunoblockade. Clinical Science (London, England:1979) Dec. 1995; 89(6):565-573.
Tan, et al. Demonstration of the neurotransmitter role of calcitonin gene-related peptides (CGRP) by immunoblockade with anti-CGRP monoclonal antibodies. Br J Pharmacol. Mar. 1994;111(3):703-10.
Tzabazis, et al. Antihyperalgesic effect of a recombinant herpes virus encoding antisense for calcitonin gene-related peptide. Anesthesiology. Jun. 2007;106(6):1196-203.
Vajdos, et al. Comprehensive functional maps of the antigen-binding site of an anti-ErbB2 antibody obtained with shotgun scanning mutagenesis. J Mol Biol. Jul. 5, 2002;320(2):415-28.
Ward, et al. Binding activities of a repertoire of single immunoglobulin variable domains secreted from Escherichia coli. Nature. Oct. 12, 1989;341(6242):544-6.
Wick, et al. Transient receptor potential vanilloid 1, calcitonin gene-related peptide, and substance P mediate nociception in acute pancreatitis. Am J Physiol Gastrointest Liver Physiol. May 2006;290(5):G959-69. Epub Jan. 6, 2006.
Wu, et al. Humanization of a murine monoclonal antibody by simultaneous optimization of framework and CDR residues. J Mol Biol. Nov. 19, 1999;294(1):151-62.
Zhang, et al. Rheumatoid factor specificity of a VH3-encoded antibody is dependent on the heavy chain CDR3 region and is independent of protein A binding. J Immunol. Sep. 1, 1998;161(5):2284-9.
Office action dated Jun. 19, 2013 for U.S. Appl. No. 13/870,871.
Seong, et al. Radiation-induced alteration of pain-related signals in an animal model with bone invasion from cancer. Ann N Y Acad Sci. Dec. 2004;1030:179-86.
U.S. Appl. No. 13/835,394, filed Mar. 25, 2013, Zeller et al.
U.S. Appl. No. 13/870,871, filed Apr. 25, 2013, Zeller et al.
U.S. Appl. No. 13/892,121, filed May 10, 2013, Poulsen et al.
U.S. Appl. No. 13/892,130, filed May 10, 2013, Poulsen et al.
Edvinsson, et al Inhibitory effect of BIBN4096BS, CGRP(8-37), a CGRP antibody and an RNA-Spiegelmer on CGRP induced vasodilatation in the perfused and non-perfused rat middle cerebral artery. Br J Pharmacol. Mar. 2007;150(5):633-40. Epub Jan. 22, 2007.
Hakala, et al. Modelling constrained calcitonin gene-related peptide analogues. Protein Eng. Feb. 1996;9(2):143-8.
Mense, S. Pathophysiology of low back pain and the transition to the chronic state-experimental data and new concepts. Schmerz. Dec. 2001;15(6):413-7.

(56) References Cited

OTHER PUBLICATIONS

Nakamura-Craig, et al. Effect of neurokinin A, substance P and calcitonin gene related peptide in peripheral hyperalgesia in the rat paw. Neurosci Lett. Mar. 11, 1991;124(1):49-51.

Office action dated Mar. 14, 2013 for U.S. Appl. No. 13/179,846.

Wacnik, et al. Tumor-induced mechanical hyperalgesia involves CGRP receptors and altered innervation and vascularization of DsRed2 fluorescent hindpaw tumors. Pain. May 2005;115(1-2):95-106.

Xu, F.T. Study on the Mechanism of SP and CGRP in the Chronic Pain and Knee Joint. Master Thesis. Guangxi Medical University. May 2005. (in Chinese with English abstract).

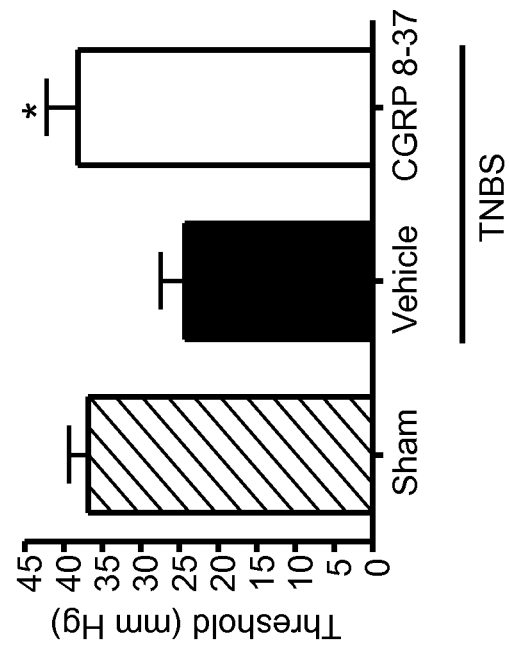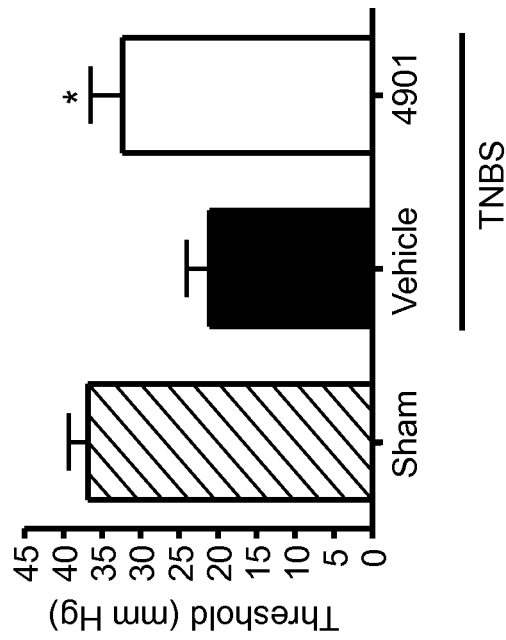

METHODS FOR TREATING VISCERAL PAIN BY ADMINISTERING ANTAGONIST ANTIBODIES DIRECTED AGAINST CALCITONIN GENE-RELATED PEPTIDE

RELATED APPLICATIONS

This application is a National Stage of PCT International Application No. PCT/IB2010/053787, filed Aug. 23, 2010, which claims the priority benefit of the provisional patent application U.S. Ser. No. 61/237,901 filed on Aug. 28, 2009, which is incorporated herein by reference in its entirety.

REFERENCE TO SEQUENCE LISTING

This application is being filed electronically and includes an electronically submitted sequence listing in .txt format. The .txt file contains a sequence listing entitled "PC33920A_SeqList.txt" created on Jan. 20, 2012 and having a size of 28 KB. The sequence listing contained in this .txt file is part of the specification and is herein incorporated by reference in its entirety.

FIELD

The invention relates to a method of treating and/or preventing visceral pain and/or symptoms of visceral pain using an anti-CGRP antibody, and to an anti-CGRP antibody for use in the prevention and/or treatment of visceral pain and/or symptoms of visceral pain.

BACKGROUND

Visceral pain is a leading cause of patient visits to the clinic, yet effective treatments for visceral pain are limited. Visceral pain is difficult to manage clinically and often requires the use of opiates. Although widely used, the severe dose-limiting adverse effects of opiates often result in diminished efficacy. Additionally, opiates carry the risk of abuse and physical dependence and induce constipation and other unwanted adverse effects, which are contraindicated in many cases and diminish quality of life.

Visceral pain is pain associated with the viscera, which encompass the internal organs of the body. These organs include, e.g., the heart, lungs, reproductive organs, bladder, ureters, the digestive organs, liver, pancreas, spleen, and kidneys. There are a variety of conditions in which visceral pain may exist, such as, for example, pancreatitis, labor, abdominal surgery associated with ileus, cystitis, menstrual period, or dysmenorrhea. Likewise, kidney pain, epigastric pain, pleural pain, and painful biliary colic, appendicitis pain may all be considered to be visceral pain. Substernal pain or pressure from early myocardial infarction is also visceral. Diseases of the stomach, duodenum or colon can cause visceral pain. Commonly encountered gastrointestinal (GI) disorders that cause visceral pain include functional bowel disorder (FBD) and inflammatory bowel disease (IBD). These GI disorders include a wide range of disease states that are currently only moderately controlled, including, with respect to FBD, gastro-esophageal reflux, dyspepsia, irritable bowel syndrome (IBS) and functional abdominal pain syndrome (FAPS), and, with respect to IBD, Crohn's disease, ileitis and ulcerative colitis, all of which regularly produce visceral pain.

IBS affects 10-20% of adults and adolescents worldwide (Longstreth et al., 2006, Gastroenterology 130(5):1480-91). The primary reason these patients seek medical attention is chronic visceral pain believed to be due to enhanced visceral sensitivity (Aziz, 2006, Gastroenterology 131(2):661-4). Patients with IBS have been shown to have a lower visceral sensory threshold to colorectal distension and that this is highly correlated to the visceral pain symptoms (Delafoy et al, 2006, Gut 55(7):940-5). Colorectal distension after trinitrobenzene sulfonic acid (TNBS) induced colitis in rats is an animal model that has been used by many researchers to explore the mechanisms of visceral hypersensitivity (Gay et al, 2006, Neuroimmunomodulation 23; 13(2):114-121; Delafoy et al, 2006; Adam et al., 2006, Pain 123(1-2):179-86).

Interstitial cystitis (IC) is a painful bladder syndrome characterized in the clinic by urinary urgency, frequency and chronic pelvic pain. Clinical studies indicate that this involves visceral sensory afferent nerve hypersensitivity where the sensation of bladder fullness occurs at lower than patients indicates an increase in nerve density in the submucosa of the bladder and evidence of neurogenic inflammation further normal volumes and bladder fullness is perceived as painful. Histopathology of IC suggests the involvement of visceral afferents.

Visceral pain can be produced in response to, for example, inflammation, distention, or increased pressure. It is not always elicited by visceral injury. In addition, visceral pain is diffuse, may be referred to other locations; and may be associated with other autonomic and motor reflexes (e.g., nausea, lower-back muscle tension from renal colic) (Lancet 1999, 353, 2145-48).

CGRP (calcitonin gene-related peptide) is a 37 amino acid neuropeptide, which belongs to a family of peptides that includes calcitonin, adrenomedullin and amylin. In humans, two forms of CGRP (α-CGRP and β-CGRP) exist and have similar activities. They vary by three amino acids and exhibit differential distribution. At least two CGRP receptor subtypes may also account for differential activities. CGRP is a neurotransmitter in the central nervous system, and has been shown to be a potent vasodilator in the periphery, where CGRP-containing neuronal processes are closely associated with blood vessels. CGRP-mediated vasodilatation is also associated with neurogenic inflammation, as part of a cascade of events that results in extravasation of plasma and vasodilation of the microvasculature and is present in migraine.

Spinally administered small molecule selective CGRP antagonists have been shown to be useful in the treatment of neuropathic and nociceptive pain conditions (Adwanikar et al, Pain, 2007, 132(1-2):53-66) suggesting that removal of endogenous CGRP signalling in the spinal cord has an antinociceptive effect. Reports have established that blocking CGRP signalling is effective in reversing visceral hypersensitivity (VH) by systemically injecting CGRP 8-37, a CGRP receptor antagonist (Delafoy et al., 2006; Plourde et al., 1997, Am J. Physiol. 273(1 Pt 1):G191-6; Julia and Bueno, 1997, Am J. Physiol. 272(1 Pt 1):G141-6). However, CGRP 8-37 has a very short half-life in-vivo and would therefore not be a useful therapeutic. Thus, there is a critical medical need to identify new therapeutics for the treatment and prevention of visceral pain.

Throughout this application various publications (including patents and patent applications) are referenced. The disclosures of these publications in their entireties are hereby incorporated by reference.

SUMMARY OF THE INVENTION

The present invention provides a method for preventing and/or treating visceral pain and/or symptoms of visceral pain in an individual, the method comprising administering a therapeutically effective amount of an anti-CGRP antagonist antibody to an individual suffering from or at risk for visceral pain.

In some embodiments, the anti-CGRP antagonist antibody administered peripherally. In other embodiments, the anti-CGRP antagonist antibody is administered orally, sublingually, via inhalation, transdermally, subcutaneously, intravenously, intra-arterially, intra-articularly, peri-articularly, locally and/or intramuscularly.

In some embodiments, the visceral pain is associated with a functional bowel disorder (FBD). The FBD may be gastroesophageal reflux, dyspepsia, irritable bowel syndrome (IBS) and functional abdominal pain syndrome (FAPS). In some embodiments, the visceral pain is associated with inflammatory bowel disease (IBD). The IBD may be Crohn's disease, ileitis or ulcerative colitis. In some embodiments, the visceral pain is associated with renal colic, dysmenorrhea, cystitis, menstrual period, labor, menopause, prostatitis or pancreatitis. In some embodiments, the visceral pain is associated interstitial cystitis (IC).

In some embodiments, the anti-CGRP antagonist antibody binds to CGRP; blocks CGRP from binding to its receptor; blocks or decreases CGRP receptor activation; inhibits blocks, suppresses or reduces CGRP biological activity; increases clearance of CGRP; and/or inhibits CGRP synthesis, production or release.

In some embodiments, the anti-CGRP antagonist antibody is a human antibody or a humanized antibody. In some embodiments, the anti-CGRP antagonist antibody is a monoclonal antibody. In some embodiments, the anti-CGRP antagonist antibody can bind CGRP with a KD of 50 nM or less (as measured by surface plasmon resonance at 37° C. and/or has a half life in-vivo of at least 7 days).

In some embodiments, the anti-CGRP antagonist antibody specifically binds to the C-terminal region of CGRP. In some embodiments, the anti-CGRP antagonist antibody specifically recognizes the epitope defined by the sequence GSKAF (SEQ ID NO: 39). In some embodiments, the anti-CGRP antagonist antibody comprises a VH domain that is at least 90% identical in amino acid sequence to SEQ ID NO: 1 or 19.

In some embodiments, the anti-CGRP antagonist antibody comprises a VL domain that is at least 90% identical in amino acid sequence to SEQ ID NO: 2 or 20. In some embodiments, the anti-CGRP antagonist antibody further comprises a VH domain that is at least 90% identical in amino acid sequence to SEQ ID NO: 1 or 19. In other embodiments, the anti-CGRP antibody comprises at least one CDR selected from the group consisting of: (a) CDR H1 as set forth in SEQ ID NO: 3, 21, 33, 34, 36 or 37; (b) CDR H2 as set forth in SEQ ID NO: 4, 22, 35 or 38; (c) CDR H3 as set forth in SEQ ID NO: 5 or 23; (d) CDR L1 as set forth in SEQ ID NO: 6 or 24; (e) CDR L2 as set forth in SEQ ID NO: 7 or 25; (f) CDR L3 as set forth in SEQ ID NO: 8 or 26; and (g) variants of L1, L2 and H2.

In some embodiments, the anti-CGRP antibody comprises the antibody G1 heavy chain full antibody amino acid sequence shown in SEQ ID NO: 11, with or without the C-terminal lysine. In some embodiments, the anti-CGRP antibody comprises the antibody G1 light chain full antibody amino acid sequence shown in SEQ ID NO: 12. In some embodiments, the anti-CGRP antibody comprises the antibody G1 heavy chain full antibody amino acid sequence shown in SEQ ID NO: 11, with or without the C-terminal lysine; and the antibody G1 light chain full antibody amino acid sequence shown in SEQ ID NO: 12.

In some embodiments, the anti-CGRP antibody comprises the antibody G2 heavy chain full antibody amino acid sequence shown in SEQ ID NO: 29, with or without the C-terminal lysine. In some embodiments, the anti-CGRP antibody comprises the antibody G2 light chain full antibody amino acid sequence shown in SEQ ID NO: 30. In some embodiments, the anti-CGRP antibody comprises the antibody G2 heavy chain full antibody amino acid sequence shown in SEQ ID NO: 29; and the antibody G2 light chain full antibody amino acid sequence shown in SEQ ID NO: 30.

In some embodiments, the anti-CGRP antagonist antibody comprises a VH domain that is at least 90% identical in amino acid sequence to SEQ ID NO: 1 and a VL domain that is at least 90% identical in amino acid sequence to SEQ ID NO: 2. In some embodiments, the anti-CGRP antagonist antibody comprises a heavy chain produced by the expression vector with ATCC Accession No. PTA-6867. In some embodiments, the anti-CGRP antagonist antibody comprises a light chain produced by the expression vector with ATCC Accession No. PTA-6866. In some embodiments, the anti-CGRP antagonist antibody is produced by the expression vectors with ATCC Accession Nos. PTA-6867 and PTA-6866.

In some embodiments, the anti-CGRP is administered by subcutaneous or intravenous injection between once, twice, three or four times per month. In some embodiments, the anti-CGRP antagonist antibody is administered at a concentration of between 5 to 100 mg/ml. In some embodiments, the anti-CGRP antagonist antibody is administered at a concentration of between 1 to 100 mg/kg of body weight.

In some embodiments, the anti-CGRP antagonist antibody does not produce CNS impairment of motor coordination or attention. In some embodiments, the anti-CGRP antagonist antibody is not administered centrally, spinally or intrathecally. In some embodiments, the anti-CGRP antagonist antibody is not a centrally, spinally or intrathecal penetrating molecule.

In some embodiments, the anti-CGRP antagonist antibody is administered separately, sequentially or simultaneously in combination with one or more further pharmacologically active compounds. In some embodiments, the one or more further pharmacologically active compounds is/are selected from: an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine; a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, or a pharmaceutically acceptable salt thereof; a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof; a benzodiazepine having a sedative action, e.g. chlordiazepoxide, clorazepate, diazepam, flurazepam, lorazepam, oxazepam, temazepam or triazolam or a pharmaceutically acceptable salt thereof; an H1 antagonist having a sedative action, e.g. diphenhydramine, pyrilamine, promethazine, chlorpheniramine or chlorocyclizine or a pharmaceutically acceptable salt thereof; a sedative such as glutethimide, meprobamate, methaqualone or dichloralphenazone or a pharmaceutically acceptable salt thereof; a skeletal muscle relaxant, e.g. baclofen, carisoprodol, chlorzoxazone, cyclobenzaprine, methocarbamol or orphrenadine or a pharmaceutically acceptable salt thereof; an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof; an alpha-adrenergic, e.g. doxazosin, tamsulosin, clonidine or 4-amino-6,7-dimethoxy-2-(5-methanesulfonamido-1,2,3,4-tetrahydroisoquinol-2-yl)-5-(2-pyridyl)quinazoline; a tricyclic antidepressant, e.g. desipramine, imipramine, amytriptiline or nortriptiline; an anticonvulsant, e.g. carbamazepine or valproate; a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S, 3S); a muscarinic antagonist, e.g oxybutin, tolterodine, propiverine, tropsium chloride or darifenacin; a COX-2 inhibitor, e.g. celecoxib, rofecoxib or valdecoxib; a non-selective COX inhibitor (preferably with G1 protection), e.g. nitroflurbiprofen (HCT-1026); a coal-tar analgesic, in particular paracetamol; neuroleptic such as droperidol; a vanilloid receptor agonist (e.g. resinferatoxin) or antagonist (e.g. capsazepine); a beta-adrenergic such as propranolol; a local anaesthetic, such as mexiletine; a corticosteriod, such as dexamethasone; a serotonin receptor agonist or antagonist; a cholinergic (nicotinic) analgesic; Tramadol®; a PDEV inhibitor, such as sildenafil, vardenafil or taladafil; an alpha-2-delta ligand such as gabapentin or pregabalin; and a canabinoid.

The present invention further provides the use of an anti-CGRP antagonist antibody for the manufacture of a medicament for the prevention and/or treatment of visceral pain and/or symptoms of visceral pain. In some embodiments, the medicament is prepared to be peripherally administered. In some embodiments, the anti-CGRP antagonist antibody acts peripherally on administration.

The present invention further provides a pharmaceutical composition for treatment and/or prevention of visceral pain and/or symptoms of visceral pain in an individual, comprising an anti-CGRP antagonist antibody and a pharmaceutically acceptable carrier. In some embodiments the composition is prepared to be peripherally administered.

The present invention further provides a kit comprising: a pharmaceutical composition for treatment and/or prevention of visceral pain and/or symptoms of visceral pain in an individual, and instructions for the peripheral administration of a therapeutically effective amount of said pharmaceutical composition to an individual for treatment and/or prevention of visceral pain and/or symptoms of visceral pain.

BRIEF DESCRIPTION OF THE DRAWINGS

FIGS. 1A and 1B depict a visceral pain model. (A) Antibody 4901 ("4901") or PBS control ("Vehicle") was administered intravenously into animals injected with trinitrobenzene sulfonic acid (TNBS) after abdominal laparotomy. Visceral pain threshold in the animals was tested using balloon distension. Pain threshold is indicated in mm Hg (y-axis). Sham represents animals injected with a control (30% ethanol) solution instead of TNBS after laparotomy. (B) CGRP receptor antagonist CGRP 8-37 or PBS control ("Vehicle") was administered intravenously into TNBS-treated animals after abdominal laparotomy. As in (A), visceral pain threshold in the animals was tested using balloon distension, and pain threshold is indicated in mm Hg (y-axis).

DETAILED DESCRIPTION OF THE INVENTION

Figure 2:
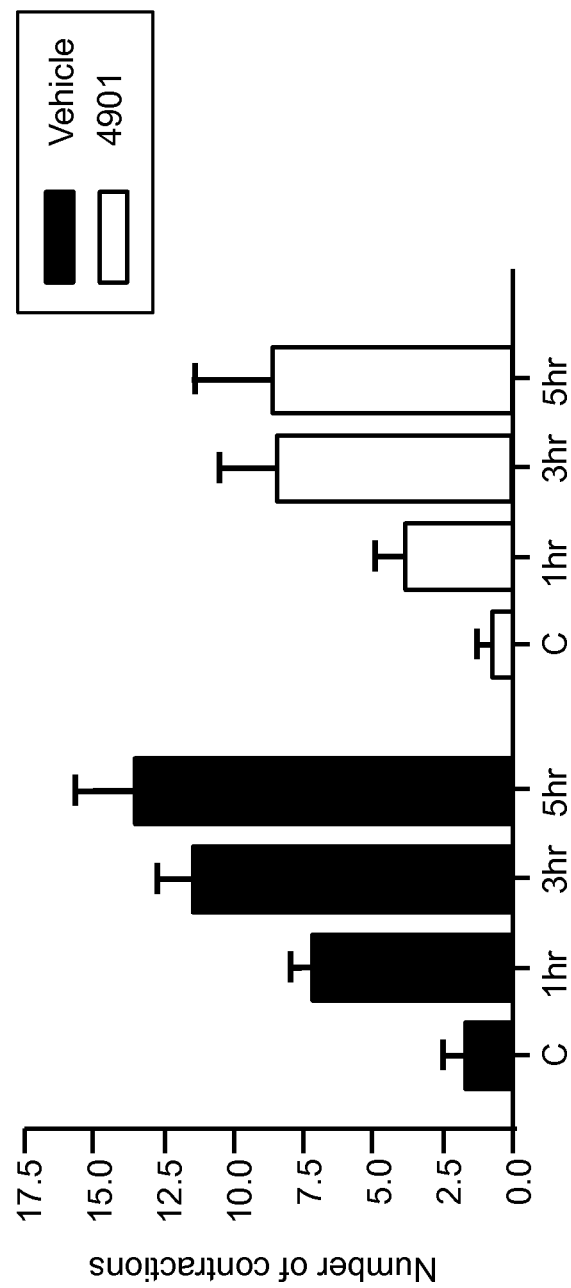
FIG. 2 depicts a visceral pain model. Antibody 4901 ("4901") or PBS control ("Vehicle") was administered intravenously into animals. Bladder motility, measured as number of contractions (y-axis), was tested at 1 h, 3 h and 5 h after turpentine-induced bladder inflammation.

The invention disclosed herein provides methods for treating and/or preventing visceral pain in an individual by administering to the individual a therapeutically effective amount of an anti-CGRP antagonist antibody.

The invention disclosed herein also provides anti-CGRP antagonist antibodies and polypeptides derived from G1 or its variants shown in Table 6 of WO2007/054809, which is hereby incorporated by reference in its entirety. The invention also provides methods of making and using these antibodies and polypeptides. Table 6 of WO2007/054809 is reproduced below:

TABLE 6

| Clone | L1 | L2 | H2 | HC-FW3 | α-rat $k_{off}$(1/s) | α-rat $K_D$ (nM) | α-human $k_{off}$(1/s) | α-human $K_D$ (nM) |
| --- | --- | --- | --- | --- | --- | --- | --- | --- |
| G1 | | | | | $3.99 \times 10^{-4}$ | 2.57 | $3.63 \times 10^{-5}$ | 0.063 |
| M1 | | | | A100L | $1.10 \times 10^{-3}$ | | $1.73 \times 10^{-4}$ | |
| M2 | | | | L99A A100R | $2.6 \times 10^{-3}$ | 58 | $3.1 \times 10^{-4}$ | 3 |
| M3 | | | | L99A A100S | $2.0 \times 10^{-3}$ | 61 | $2.1 \times 10^{-4}$ | 1.7 |
| M4 | | | | L99A A100V | $1.52 \times 10^{-3}$ | 84.4 | $6.95 \times 10^{-5}$ | 0.43 |
| M5 | | | | L99A A100Y | $7.35 \times 10^{-4}$ | 40.8 | $3.22 \times 10^{-5}$ | 0.20 |
| M6 | | | | L99N | $7.84 \times 10^{-4}$ | 43.6 | $1.33 \times 10^{-4}$ | 0.83 |
| M7 | | | | L99N A100C | $9.18 \times 10^{-4}$ | 51.0 | $2.43 \times 10^{-4}$ | 1.52 |
| M8 | | | | L99N A100G | $7.45 \times 10^{-4}$ | 41.4 | $9.20 \times 10^{-5}$ | 0.58 |
| M9 | | | | L99N A100Y | n.d. | n.d. | $1.00 \times 10^{-5}$ | 0.06 |
| M10 | | | | L99S A100S | $1.51 \times 10^{-3}$ | 83.9 | $1.73 \times 10^{-4}$ | 1.08 |
| M11 | | | | L99S A100T | $4.83 \times 10^{-3}$ | 268.3 | $2.83 \times 10^{-4}$ | 1.77 |

TABLE 6-continued

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M12 | | | | L99S A100V | $1.94 \times 10^{-3}$ | 107.8 | $1.01 \times 10^{-4}$ | 0.63 |
| M13 | | | | L99T A100G | $1.84 \times 10^{-3}$ | 102.2 | $1.86 \times 10^{-4}$ | 1.16 |
| M14 | | | | L99T A100K | n.d. | n.d. | $1.00 \times 10^{-5}$ | 0.06 |
| M15 | | | | L99T A100P | $1.15 \times 10^{-3}$ | 63.9 | $1.58 \times 10^{-5}$ | 0.10 |
| M16 | | | | L99T A100S | $9.96 \times 10^{-4}$ | 55.3 | $1.65 \times 10^{-4}$ | 1.03 |
| M17 | | | | L99T A100V | $2.06 \times 10^{-3}$ | 114.4 | $1.85 \times 10^{-4}$ | 1.16 |
| M18 | | | | L99V A100G | $1.22 \times 10^{-3}$ | 67.8 | $7.03 \times 10^{-5}$ | 0.44 |
| M19 | | | | L99V A100R | n.d. | n.d. | $1.00 \times 10^{-5}$ | 0.06 |
| M20 | R28W | | | L99R A100L | $1.44 \times 10^{-3}$ | 80.0 | $1.36 \times 10^{-4}$ | 0.85 |
| M21 | R28W | | | L99S | $6.95 \times 10^{-4}$ | 15.2 | $1.42 \times 10^{-4}$ | 1.23 |
| M22 | R28W | | | L99T | $1.10 \times 10^{-3}$ | 61.1 | $1.16 \times 10^{-4}$ | 0.73 |
| M23 | R28G | | | L99T A100V | $7.99 \times 10^{-4}$ | 44.4 | $1.30 \times 10^{-4}$ | 0.81 |
| M24 | R28L | | | L99T A100V | $1.04 \times 10^{-3}$ | 57.8 | $1.48 \times 10^{-4}$ | 0.93 |
| M25 | R28N | | | L99T A100V | $1.4 \times 10^{-3}$ | 76 | $1.4 \times 10^{-4}$ | 1.3 |
| M26 | R28N | | A57G | L99T A100V | $9.24 \times 10^{-4}$ | 51.3 | $1.48 \times 10^{-4}$ | 0.93 |
| M27 | R28N T30A | | | L99T A100V | $3.41 \times 10^{-3}$ | 189.4 | $3.57 \times 10^{-4}$ | 2.23 |
| M28 | R28N T30D | | E54R A57N | L99T A100V | $1.25 \times 10^{-3}$ | 69.4 | $9.96 \times 10^{-5}$ | 0.62 |
| M29 | R28N T30G | | | L99T A100V | $3.59 \times 10^{-3}$ | 199.4 | $3.80 \times 10^{-4}$ | 2.38 |
| M30 | R28N T30G | | E54K A57E | L99T A100V | $6.38 \times 10^{-3}$ | 354.4 | $5.90 \times 10^{-4}$ | 3.69 |
| M31 | R28N T30G | | E54K A57G | L99T A100V | $3.61 \times 10^{-3}$ | 200.6 | $3.47 \times 10^{-4}$ | 2.17 |
| M32 | R28N T30G | | E54K A57H | L99T A100V | $2.96 \times 10^{-3}$ | 164.4 | $2.71 \times 10^{-4}$ | 1.69 |
| M33 | R28N T30G | | E54K A57N S58G | L99T A100V | $9.22 \times 10^{-3}$ | 512.2 | $7.50 \times 10^{-4}$ | 4.69 |
| M34 | R28N T30G | | E54K A57N S58T | L99T A100V | $2.17 \times 10^{-3}$ | 120.6 | $6.46 \times 10^{-4}$ | 4.04 |
| M35 | R28N T30G | | E54K A57S | L99T A100V | $3.99 \times 10^{-3}$ | 221.7 | $3.39 \times 10^{-4}$ | 2.12 |
| M36 | R28N T30R | | | L99T A100V | $4.79 \times 10^{-3}$ | 266.1 | $2.39 \times 10^{-4}$ | 1.49 |
| M37 | R28N T30S | | A57G | L99T A100V | $1.45 \times 10^{-3}$ | 80.6 | $2.26 \times 10^{-4}$ | 1.41 |
| M38 | R28N T30W | | | L99T A100V | $5.11 \times 10^{-3}$ | 283.9 | $2.18 \times 10^{-4}$ | 1.36 |
| M39 | R28N L56T | G50A | A57N S58Y | L99T A100V | $9.95 \times 10^{-3}$ | 552.8 | $4.25 \times 10^{-4}$ | 2.66 |
| M40 | R28N L56T | G50A | E54K A57L | L99T A100V | 0.36 | 20000.0 | $1.28 \times 10^{-3}$ | 8.00 |
| M41 | R28N L56T | G50A | E54K A57N E64D | L99T A100V | $4.53 \times 10^{-3}$ | 251.7 | $2.10 \times 10^{-4}$ | 1.31 |
| M42 | R28N L56T | G50A | E54K A57N H61F | L99T A100V | $7.52 \times 10^{-3}$ | 417.8 | $4.17 \times 10^{-4}$ | 2.61 |
| M43 | R28N L56T | G50A | E54K A57N S58C | L99T A100V | $4.53 \times 10^{-3}$ | 251.7 | $2.63 \times 10^{-4}$ | 1.64 |
| M44 | R28N L56T | G50A | E54K A57N S58E | L99T A100V | $6.13 \times 10^{-3}$ | 443 | $2.10 \times 10^{-4}$ | 2.05 |
| M45 | R28N L56T | G50A | E54K A57N S58E E64D | L99T A100V | $5.58 \times 10^{-3}$ | 259 | $2.11 \times 10^{-4}$ | 1.85 |
| M46 | R28N L56T | G50A | E54K A57N | L99T A100V | $2.94 \times 10^{-3}$ | 163.3 | $5.39 \times 10^{-4}$ | 3.37 |

TABLE 6-continued

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M47 | R28N | G50A L56T | S58E H61F E54K A57N | L99T A100V | $8.23 \times 10^{-3}$ | 457.2 | $3.32 \times 10^{-4}$ | 2.08 |
| M48 | R28N | G50A L56T | S58G E54K A57N | L99T A100V | 0.0343 | 1905.6 | $8.42 \times 10^{-4}$ | 5.26 |
| M49 | R28N | G50A L56T | S58L E54K A57N | L99T A100V | 0.0148 | 822.2 | $5.95 \times 10^{-4}$ | 3.72 |
| M50 | R28N | G50A L56T | S58Y H61F E54K A57R | L99T A100V | $5.30 \times 10^{-3}$ | 294.4 | $4.06 \times 10^{-4}$ | 2.54 |
| M51 | R28N | L56I | E54K A57G | L99T A100V | $1.18 \times 10^{-3}$ | 65.6 | $1.31 \times 10^{-4}$ | 0.82 |
| M52 | R28N | L56I | E54K A57N | L99T A100V | $2.29 \times 10^{-3}$ | 127.2 | $2.81 \times 10^{-4}$ | 1.76 |
| M53 | R28N | L56I | S58A E54K A57N | L99T A100V | $1.91 \times 10^{-3}$ | 106.1 | $3.74 \times 10^{-4}$ | 2.34 |
| M54 | R28N T30A | G50A | S58G E54K A57N | L99T A100V | $2.16 \times 10^{-3}$ | 120.0 | $1.79 \times 10^{-3}$ | 11.19 |
| M55 | R28N T30A | G50A L56S | S58P E54K A57N | L99T A100V | $5.85 \times 10^{-3}$ | 325.0 | $4.78 \times 10^{-4}$ | 2.99 |
| M56 | R28N T30D | L56S | S58E E64D E54K A57N | L99T A100V | $9.35 \times 10^{-3}$ | 519.4 | $4.79 \times 10^{-4}$ | 2.99 |
| M57 | R28N T30D | L56S | H61F E54K A57N | L99T A100V | 0.0104 | 1.200 | $3.22 \times 10^{-4}$ | 3.08 |
| M58 | R28N T30D | L56S | S58E E54K A57N | L99T A100V | No binding | n.d. | $1.95 \times 10^{-3}$ | 12.19 |
| M59 | R28N T30D | L56S | S58I H61F E54K A57N | L99T A100V | 0.0123 | 683.3 | $5.24 \times 10^{-4}$ | 3.28 |
| M60 | R28N T30D | L56S | S58N H61F E54K A57N | L99T A100V | 0.0272 | 1511.1 | $9.11 \times 10^{-4}$ | 5.69 |
| M61 | R28N T30G | A51H | S58R H61F E54Q A57N | L99T A100V | $5.21 \times 10^{-3}$ | 289.4 | $4.59 \times 10^{-4}$ | 2.87 |
| M62 | R28N T30G | A51H L56T | H61F E54K A57N | L99T A100V | $5.75 \times 10^{-3}$ | 242 | $5.57 \times 10^{-4}$ | 5.86 |
| M63 | R28N T30G | G50A | S58E E54K A57N | L99T A100V | $2.65 \times 10^{-3}$ | 147.2 | $1.50 \times 10^{-3}$ | 9.38 |
| M64 | R28N T30G | G50A | S58T E54K A57N | L99T A100V | 0.0234 | 1300.0 | $1.32 \times 10^{-3}$ | 8.25 |
| M65 | R28N T30G | G50A L56I | S58V E54K A57C | L99T A100V | $4.07 \times 10^{-3}$ | 226.1 | $8.03 \times 10^{-4}$ | 5.02 |
| M66 | R28N T30G | L56I | E54K A57E | L99T A100V | $5.11 \times 10^{-3}$ | 283.9 | $5.20 \times 10^{-4}$ | 3.25 |
| M67 | R28N T30G | L56I | E54K A57F | L99T A100V | $1.71 \times 10^{-3}$ | 95.0 | $8.20 \times 10^{-4}$ | 5.13 |
| M68 | R28N T30G | L56I | E54K A57N | L99T A100V | $6.76 \times 10^{-3}$ | 375.6 | $4.28 \times 10^{-4}$ | 2.68 |
| M69 | R28N T30G | L56I | S58D E64D E54K A57N | L99T A100V | $1.81 \times 10^{-3}$ | 100.6 | $7.33 \times 10^{-4}$ | 4.58 |
| M70 | R28N T30G | L56I | S58E E54K A57S | L99T A100V | $6.07 \times 10^{-3}$ | 337.2 | $5.59 \times 10^{-4}$ | 3.49 |
| M71 | R28N T30G | L56I | E54K A57Y | L99T A100V | $2.12 \times 10^{-3}$ | 117.8 | $1.28 \times 10^{-3}$ | −8.00 |

TABLE 6-continued

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M72 | R28N T30G | L56S | E54K | L99T A100V | $3.95 \times 10^{-3}$ | 219.4 | $4.00 \times 10^{-4}$ | 2.50 |
| M73 | R28N T30G | L56S | E54K A57N S58Y E64D | L99T A100V | $3.00 \times 10^{-3}$ | 166.7 | $2.55 \times 10^{-4}$ | 1.59 |
| M74 | R28N T30G | L56S | E54K A57S | L99T A100V | $6.03 \times 10^{-3}$ | 335.0 | $5.97 \times 10^{-4}$ | 3.73 |
| M75 | R28N T30G | L56S | E54K A57V | L99T A100V | $1.87 \times 10^{-2}$ | 1038.9 | $1.16 \times 10^{-3}$ | 7.25 |
| M76 | R28N T30S | G50A L56T | A57G | L99T A100V | $1.16 \times 10^{-3}$ | 64.4 | $3.64 \times 10^{-4}$ | 2.28 |
| M77 | R28N T30S | G50A L56T | E54K A57D | L99T A100V | 0.0143 | 794.4 | $4.77 \times 10^{-4}$ | 2.98 |
| M78 | R28N T30S | G50A L56T | E54K A57N S58T | L99T A100V | 0.167 | 9277.8 | $1.31 \times 10^{-3}$ | 8.19 |
| M79 | R28N T30S | G50A L56T | E54K A57P | L99T A100V | 0.19 | 10555.6 | $1.29 \times 10^{-3}$ | 8.06 |
| M80 | R28N T30S | L56I | E54K A57N S58V | L99T A100V | 0.0993 | 5516.7 | $2.09 \times 10^{-3}$ | 13.06 |
| M81 | R28N T30S | L56S | E54K A57N S58E | L99T A100V | $4.29 \times 10^{-3}$ | 238.3 | $4.90 \times 10^{-4}$ | 3.06 |
| M82 | R28N T30V | A51H L56T | A57N | L99T A100V | $6.99 \times 10^{-3}$ | 388.3 | $8.77 \times 10^{-4}$ | 5.48 |
| M83 | R28N T30V | A51H L56T | E54K A57N S58M H61F | L99T A100V | No binding | n.d. | $9.33 \times 10^{-4}$ | 5.83 |
| M84 | R28N T30V | A51H L56T | E54K A57N | L99T A100V | $1.76 \times 10^{-2}$ | 977.8 | $1.08 \times 10^{-3}$ | 6.75 |

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains (e.g., a heavy chain variable domain and a light chain variable domain), in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77, 1985; Boerner et al., 1991, J. Immunol., 147 (1):86-95; and U.S. Pat. No. 5,750,373.

As used herein, the term "calcitonin gene-related peptide" and "CGRP" refers to any form of calcitonin gene-related peptide and variants thereof that retain at least part of the activity of CGRP. For example, CGRP may be α-CGRP or β-CGRP. As used herein, CGRP includes all mammalian species of native sequence CGRP, e.g., human, canine, feline, equine, and bovine.

As used herein, an "anti-CGRP antagonist antibody" (interchangeably termed "anti-CGRP antibody") refers to an antibody that is able to bind to CGRP and inhibit CGRP biological activity and/or downstream pathway(s) mediated by CGRP signaling. An anti-CGRP antagonist antibody encompasses antibodies that block, antagonize, suppress or reduce (including significantly) CGRP biological activity, including downstream pathways mediated by CGRP signaling, such as receptor binding and/or elicitation of a cellular response to CGRP. For purpose of the present invention, it will be explicitly understood that the term "anti-CGRP antagonist antibody" encompasses all the previously identified terms, titles, and functional states and characteristics whereby the CGRP itself, a CGRP biological activity (including but not limited to its ability to mediate any aspect of visceral pain), or the consequences of the biological activity, are substantially nullified, decreased, or neutralized in any meaningful degree. In some embodiment, an anti-CGRP antagonist antibody binds CGRP and prevents CGRP binding to a CGRP receptor. In other embodiments, an anti-CGRP antibody binds CGRP and prevents activation of a CGRP receptor. Examples of anti-CGRP antagonist antibodies are provided herein.

As used herein, the terms "G1" and "antibody G1" are used interchangeably to refer to an antibody produced by the expression vectors having deposit numbers ATCC-PTA-6867 and ATCC-PTA-6866. The amino acid sequence of the heavy chain and light chain variable regions are shown in SEQ ID NOs: 1 and 2. The CDR portions of antibody G1 (including Chothia and Kabat CDRs) are diagrammatically depicted in FIG. 5 of WO2007/054809, the content of which is herein incorporated by reference in its entirety. The polynucleotides encoding the heavy and light chain variable regions are shown in SEQ ID NOs: 9 and 10. The characterization of antibody G1 is described in the Examples of WO2007/054809.

As used herein, the terms "G2" and "antibody G2" are used interchangeably to refer to an anti-rat CGRP mouse monoclonal antibody as described in Wong H C et al. Hybridoma 12:93-106, 1993. The amino acid sequence of the heavy chain and light chain variable regions are shown in SEQ ID NOs: 19 and 20. The polynucleotides encoding the heavy and light chain variable regions are shown in SEQ ID NOs: 27 and 28. The CDR portions of antibody G2 are provided in SEQ ID NOs: 21 to 26.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CGRP epitope is an antibody that binds this epitope with greater affinity, avidity, more readily, and/or with greater duration than it binds to other CGRP epitopes or non-CGRP epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected with a polynucleotide(s) of this invention.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus of the heavy chain. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, at least about 99% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. Nos. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

As used herein, "treatment" is an approach for obtaining beneficial or desired clinical results. For purposes of this invention, beneficial or desired clinical results include, but are not limited to, one or more of the following: improvement in any aspect of visceral pain including lessening severity, alleviation of pain intensity, and other associated symptoms, reducing frequency of recurrence, increasing the quality of life of those suffering from the visceral pain, and decreasing dose of other medications required to treat the visceral pain. Other associated symptoms include, but are not limited to, cramps, aches, diffuse pain, pressure, fullness, squeezing, nausea, vomiting, and sensitivity to light, sound, and/or movement.

"Reducing incidence" of visceral pain means any of reducing severity (which can include reducing need for and/or amount of (e.g., exposure to) other drugs and/or therapies generally used for this condition, including, for example, opiates (e.g., oxycodone, morphine, butorphanol, nalbuphine, etc.), duration, and/or frequency. As is understood by those skilled in the art, individuals may vary in terms of their response to treatment, and, as such, for example, a "method of reducing incidence of visceral pain in an individual" reflects administering the anti-CGRP antagonist antibody based on a reasonable expectation that such administration may likely cause such a reduction in incidence in that particular individual.

"Ameliorating" visceral pain and/or a symptom associated with visceral pain means a lessening or improvement of one or more symptoms of visceral pain and/or symptoms associated with visceral pain as compared to not administering an anti-CGRP antagonist antibody. "Ameliorating" also includes shortening or reduction in duration of a symptom.

"Palliating" visceral pain and/or a symptom associated with visceral pain means lessening the extent of one or more undesirable clinical manifestations of visceral pain in an individual or population of individuals treated with an anti-CGRP antagonist antibody in accordance with the invention.

As used herein, "controlling visceral pain" refers to maintaining or reducing severity or duration of one or more symptoms of visceral pain or frequency of visceral pain as compared to the level before treatment. For example, the duration or severity of visceral pain, or frequency of visceral pain, can be reduced by at least about any of 10%, 20%, 30%, 40%, 50%, 60%, or 70% in the individual as compared to the level before treatment.

As used therein, "delaying" the development of visceral pain means to defer, hinder, slow, retard, stabilize, and/or postpone progression of the visceral pain. This delay can be of varying lengths of time, depending on the history of the disease and/or individuals being treated. As is evident to one skilled in the art, a sufficient or significant delay can, in effect, encompass prevention, in that the individual does not develop visceral pain. A method that "delays" development of the symptom is a method that reduces probability of developing the symptom in a given time frame and/or reduces extent of the symptoms in a given time frame, when compared to not using the method. Such comparisons are typically based on clinical studies, using a number of subjects sufficient to show a statistically significant difference between treated and untreated subjects.

"Development" or "progression" of visceral pain means initial manifestations and/or ensuing progression of the disorder. Development of visceral pain can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of visceral pain includes initial onset and/or recurrence.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing pain intensity, duration, or frequency of visceral pain attack, and decreasing one or more symptoms resulting from visceral pain (biochemical, histological and/or behavioral), including its complications and intermediate pathological phenotypes presenting during development of the pain, increasing the quality of life of those suffering from the pain, decreasing the dose of other medications required to treat the pain, enhancing effect of another medication, and/or delaying the progression of the pain of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably a human. Mammals also include, but are not limited to, farm animals, sport animals, pets, primates, horses, dogs, cats, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

Methods for Preventing or Treating Visceral Pain

Disclosed herein are methods for the prevention and/or treatment of visceral pain and/or symptoms of visceral pain and a medicament for prevention and/or treatment of visceral pain and/or one or more symptoms of visceral pain in an individual.

In some embodiments, the invention provides a method of preventing and/or treating visceral pain and/or one or more symptoms of visceral pain in an individual, comprising peripheral administration to the individual of an effective amount of an anti-CGRP antagonist antibody.

In other embodiments, the invention provides a method of ameliorating, controlling, reducing incidence of, or delaying the development or progression of visceral pain and/or one or more symptoms of visceral pain in an individual, comprising peripheral administration to the individual of an effective amount of an anti-CGRP antagonist antibody.

In some embodiments, the invention provides the use of an anti-CGRP antagonist antibody for the manufacture of a medicament for the prevention and/or treatment of visceral pain and/or one or more symptoms of visceral pain, wherein the medicament is prepared for peripheral administration or wherein the medicament is administered peripherally.

In other embodiments, the invention provides an anti-CGRP antagonist antibody for use in the prevention and/or treatment of visceral pain and/or symptoms of visceral pain wherein the antibody is prepared for peripheral administration or wherein the antibody is administered peripherally.

In other embodiments, the invention provides the use of an anti-CGRP antagonist antibody for the manufacture of a medicament for ameliorating, controlling, reducing incidence of, or delaying the development or progression of visceral pain and/or symptoms of visceral pain, wherein the medicament is prepared for peripheral administration or wherein the medicament is administered peripherally.

In some embodiments, the individual is preferably a mammal, for example a companion animal such as a horse, cat or dog or a farm animal such as a sheep, cow or pig. Most preferably the mammal is a human.

In some embodiments, the medicament and/or anti-CGRP antagonist antibody is prepared for oral, sublingual, buccal, topical, rectal, inhalation, transdermal, subcutaneous, intravenous, intra-arterial, intramuscular, intracardiac, intraosseous, intradermal, intraperitoneal, transmucosal, vaginal, intravitreal, intra-articular, peri-articular, central, local or epicutaneous administration.

In some embodiments, the medicament is prepared for peripheral administration prior to and/or during and/or after the development of visceral pain.

In some embodiments, the anti-CGRP antagonist antibody acts peripherally on administration. In one embodiment, the anti-CGRP antagonist antibody is not administered centrally, spinally or intrathecally.

In some embodiments, the visceral pain is associated with and/or caused by a disease such as, for example, a functional bowel disorder (FBD) or inflammatory bowel disease (IBD). In embodiments where the visceral pain is associated with FBD, the FBD may be, for example without limitation, gastro-esophageal reflux, dyspepsia, irritable bowel syndrome (IBS) or functional abdominal pain syndrome (FAPS). Most preferably, the disease is IBS. In embodiments where the visceral pain is associated with IBD, the IBD may be, for example without limitation, Crohn's disease, ileitis or ulcerative colitis. Other types of visceral pain include the pain associated with, for example, cancer, renal colic, dysmenorrhea, cystitis, including interstitial cystitis (IC), surgery associated with the ileus, menstrual period, labor, menopause, bone fracture, diverticulitis, peritonitis, pericarditis, hepatitis, appendicitis, colitis, cholecystitis, endometriosis, chronic and/or acute pancreatitis, myocardial infarction, kidney pain, pleural pain, prostatitis, pelvic pain, and trauma to an organ.

In some embodiments, the methods and uses of the invention may be for ameliorating visceral pain and/or one or more symptoms associated with visceral pain in an individual having FBD, IBD or IC.

Diagnosis or assessment of visceral pain is well-established in the art. Assessment may be performed based on measures known in the art, such as patient characterization of pain using various pain scales. See, e.g., Katz et al, *Surg Clin North Am.*, 1999, 79 (2):231-52; Caraceni et al. *J Pain Symptom Manage*, 2002, 23(3):239-55. For example, the verbal descriptor scale (VDS), the visual analog scale (VAS), the Prince Henry Hospital Pain Scale (PHHPS), the numeric rating scale (NRS), and the Faces Pain Scale, and variations thereof, may be employed to assess pain and evaluate response to the treatment. There are also commonly used scales to measure disease state such as the Functional Bowel Disorder Severity Index (FBDSI) (Drossman et al., 1995, *Digestive Diseases and Sciences* 40(5):986-995) and the IBS Severity Scoring System (Francis et al., 1997, Aliment Pharmacol Ther., 11(2):395-402). Such scales may be employed to evaluate response to the treatment.

In some embodiments, ameliorating, controlling, reducing incidence of, or delaying the development or progression of FBD pain and/or symptoms of FBD pain is measured by one or more of the FBDSI, VDS, VAS, PHHPS, NRS and Faces Pain Scale. In another embodiment, ameliorating, controlling, reducing incidence of, or delaying the development or progression of IBS pain and/or symptoms of IBS pain is measured by one or more of the IBS Severity Scoring System, VDS, VAS, PHHPS, NRS and Faces Pain Scale.

In some embodiments, ameliorating, controlling, reducing incidence of, or delaying the development or progression of IC pain and/or symptoms of IC pain is measured by one or more of the VDS, VAS, PHHPS, NRS and Faces Pain Scale.

Anti-CGRP Antagonist Antibodies

In some embodiments, the anti-CGRP antagonist antibody binds to CGRP. Preferably, the anti-CGRP antagonist antibody binds to CGRP and inhibits the ability of CGRP to bind to the CGRP receptor. In some embodiments, the anti-CGRP antagonist antibody binds to both human and rodent CGRP, preferably human and rat CGRP. More preferably, the antibody binds to human CGRP. In preferred embodiments, the anti-CGRP antagonist antibody binds to human α-CGRP or to human α-CGRP and/or β-CGRP. Most preferably, the anti-CGRP antagonist antibody is an antibody that exhibits any one or more of the following functional characteristics: (a) binds to CGRP; (b) blocks CGRP from binding to its receptor(s); (c) blocks or decreases CGRP receptor activation, including cAMP activation; (d) inhibits, blocks, suppresses or reduces CGRP biological activity, including downstream pathways mediated by CGRP signalling, such as receptor binding and/or elicitation of a cellular response to CGRP; (e) prevents, ameliorates, or treats any aspect of visceral pain; (f) increases clearance of CGRP; and (g) inhibits (reduces) CGRP synthesis, production or release.

In some embodiments, the anti-CGRP antagonist antibody binds to a fragment of CGRP, more preferably to a fragment of CGRP as well as to the full length CGRP. Preferably, the anti-CGRP antagonist antibody binds to the C-terminal region or fragment of CGRP. The C-terminal region or fragment of CGRP preferably comprises amino acids 19-37 or 25-37 or 29-37, or, alternatively, amino acids 30-37, or, further alternatively, amino acids 31-37 of CGRP. In a further embodiment, the C-terminal region or fragment of CGRP preferably comprises amino acids 32-37, most preferably amino acids 33-37 of CGRP. Preferably, the CGRP is either α-CGRP or β-CGRP, further preferably human or rodent, further preferably human or rat, more preferably human, further preferably human α-CGRP or β-CGRP, most preferably human α-CGRP.

In some embodiments, the anti-CGRP antagonist antibody specifically binds to the amino acid sequence GSKAF (SEQ ID NO: 39). Preferably the sequence GSKAF (SEQ ID NO: 39) of CGRP is the epitope to which the anti-CGRP antagonist antibody binds.

In some embodiments, an anti-CGRP antagonist antibody is provided which specifically binds to an epitope defined by amino acids G33 to F37 of CGRP. The anti-CGRP antagonist antibody may specifically bind to the epitope defined by the amino acid sequence GSKAF (SEQ ID NO: 39). In some embodiments, the present invention provides the use of such an antibody in the uses and methods defined in the various aspects of the present invention.

In some embodiments, the anti-CGRP antagonist antibody inhibits or prevents activation of the CGRP receptor. Preferably the anti-CGRP antibody has an $IC_{50}$ of between about 0.0001 (0.1 nM) to about 500 µM. In some preferred embodiments, the IC50 is between about 0.0001 µM and any of about 250 µM, 100 µM, 50 µM, 10 µM, 1 µM, 500 nM, 250 nM, 100 nM, 50 nM, 20 nM, 15 nM, 10 nM, 5 nM, 1 nM, or 0.5 nM as measured in an in vitro binding assay. In some further preferred embodiments, IC50 is less than any of about 500 pM, or about 100 pM, or about 50 pM, as measured in an in vitro binding assay. In a further more preferred embodiment IC50 is about 1.2 nM or 31 nM.

In some embodiments, the anti-CGRP antagonist antibody used is capable of competing with an antibody herein above described for the binding of CGRP or to a fragment of CGRP, or to a fragment of CGRP as well as the full length CGRP, preferably to the C-terminal region or fragment of CGRP. In preferred embodiments, the C-terminal region or fragment of CGRP comprises amino acids 19-37, 25-37, 29-37, 30-37, or 31-37 of CGRP. In a further embodiment, the C-terminal region or fragment of CGRP preferably comprises amino acids 32-37, most preferably 33-37, of CGRP.

In some embodiments, the anti-CGRP antagonist antibody binds to CGRP, a region of CGRP, or a fragment of CGRP with a binding affinity ($K_D$) of between about 0.00001 µM (0.01 nM) to about 500 µM. In some embodiments, the binding affinity ($K_D$) is between about 0.00001 µM and any of about 250 µM, 100 µM, 50 µM, 10 µM, 1 µM, 500 nM, 250 nM, 100 nM, 50 nM, 20 nM, 15 nM, 10 nM, 5 nM, 1 nM, 0.5 nM, 1 nM, 0.05 nM, or 0.01 nM as measured in an in vitro binding assay. In some embodiments, the binding affinity ($K_D$) is less than any of about 500 µM, or 100 µM, 50 µM, or 10 µM, as measured in an in vitro binding assay. In further more preferred embodiments, binding affinity ($K_D$) is about 0.04 nM or 16 nM.

The anti-CGRP antagonist antibody as used in the present invention may be selected from the group of: monoclonal antibodies, polyclonal antibodies, antibody fragments (e.g., Fab, Fab', F(ab')2, Fv, Fc, ScFv etc.), chimeric antibodies, bispecific antibodies, heteroconjugate antibodies, single chain (ScFv) antibodies, mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The anti-CGRP antagonist antibody may be murine, rat, human, or any other origin (including chimeric or humanized antibodies). In some embodiments, the anti-CGRP antagonist antibody may be humanized but is more preferably human. In some embodiments, the anti-CGRP antagonist antibody is isolated. In some embodiments, the anti-CGRP antagonist antibody is substantially pure. Where the anti-CGRP antagonist antibody is an antibody fragment, the fragment preferably retains the functional characteristics of the original antibody, i.e., the CGRP binding and/or antagonist activity as described in the functional characteristics above.

Examples of anti-CGRP antagonist antibodies are known in the art. Hence, according to a preferred embodiment of the present invention the anti-CGRP antagonist antibody as used in the present invention is preferably an anti-CGRP antibody as generally or specifically disclosed in any of (i) WO2007/054809, (ii) WO2007/076336, (iii) Tan et al., Clin. Sci. (Lond). 89:565-73, 1995, (iv) Sigma (Missouri, US), product number C7113 (clone #4901), (v) Plourde et al., Peptides 14:1225-1229, 1993, or which comprises or consists of:

(a) a fragment of said antibody (e.g., Fab, Fab', F(ab')2, Fv, Fc, ScFv etc.),
(b) a light chain of said antibody,
(c) a heavy chain of said antibody,
(d) one or more variable region(s) from a light chain and/or a heavy chain of said antibody,
(e) one or more CDR(s) (one, two, three, four, five or six CDRs) of said antibody,
(f) CDR H3 from the heavy chain of said antibody,
(g) CDR L3 from the light chain of said antibody,
(h) three CDRs from the light chain of said antibody,
(i) three CDRs from the heavy chain of said antibody,
(j) three CDRs from the light chain and three CDRs from the heavy chain, of said antibody,
(k) any one or more of (a) through (j).

In some embodiments, the anti-CGRP antagonist antibody is antibody G2 or antibody G1. According to a most preferred embodiment of the present the anti-CGRP antagonist antibody used is the anti-CGRP antibody G1 as specifically disclosed in PCT Patent Application Pub. No. WO2007/054809, or comprising its variants shown in Table 6 of WO2007/054809, also including functionally equivalent antibodies to G1, i.e., comprising conservative substitutions of amino acid residues or one or more deletions or additions of amino acids which do not significantly affect their functional characteristics e.g. CGRP binding or antagonist activity and variants which have enhanced or decreased activity and/or binding. As used herein, the terms "G1" and "antibody G1" are used interchangeably to refer to an antibody produced by expression vectors having deposit numbers of ATCC PTA-6867 and ATCC PTA-6866 as disclosed in application WO2007/054809. Functional characteristics of antibody G1 are described in PCT Patent Application Nos. PCT/IB2009/050849 and PCT/IB2009/050852, both filed Mar. 3, 2009, and incorporated herein by reference in their entireties.

According to a further embodiment of the present invention, the anti-CGRP antagonist antibody comprises or consists of a polypeptide selected from: (a) antibody G1 or its variants shown in Table 6 of WO2007/054809; (b) a fragment or a region of antibody G1 or its variants shown in Table 6 of WO2007/054809; (c) a light chain of antibody G1 or its variants shown in Table 6 of WO2007/054809; (d) a heavy chain of antibody G1 or its variants shown in Table 6 of WO2007/054809 (e) one or more variable region(s) from a light chain and/or a heavy chain of antibody G1 or its variants shown in Table 6 of WO2007/054809; (f) one or more CDR(s) (one, two, three, four, five or six CDRs) of antibody G1 or its variants shown in Table 6 of WO2007/054809; (g) CDR H3 from the heavy chain of antibody G1 or its variants shown in Table 6 of WO2007/054809; (h) CDR L3 from the light chain of antibody G1 or its variants shown in Table 6 of WO2007/054809; (i) three CDRs from the light chain of antibody G1 or its variants shown in Table 6 of WO2007/054809; (j) three CDRs from the heavy chain of antibody G1 or its variants shown in Table 6 of WO2007/054809; (k) three CDRs from the light chain and/or three CDRs from the heavy chain, of antibody G1 or its variants shown in Table 6 of WO2007/054809; and (i) an antibody comprising any one of (b) through (k). The invention also provides polypeptides comprising any one or more of the above. In some embodiments, the at least one, two, three, four, five, or six CDR(s) are at least about 85%, 86%, 87%, 88%, 89%, 90%, 91%, 92%, 93%, 94%, 95%, 96%, 97%, 98%, or 99% identical to at least one, two, three, four, five or six CDRs of G1 or its variants shown in Table 6 of WO2007/054809. Determination of CDR regions is well within the ability of the skilled person. It is understood that in some embodiments, CDRs can be a combination of the Kabat and Chothia CDR. In some embodiments, the CDRs are the Kabat CDRs. In other embodiments, the CDRs are the Chothia CDRs.

The anti-CGRP antagonist antibody preferably comprises or consists of a fragment or a region of the antibody G1 (e.g., Fab, Fab', F(ab')2, Fv, Fc, ScFv etc.) or its variants shown in Table 6 of WO2007/054809. Preferably, said fragment or region has the functional characteristics of an anti-CGRP antagonist antibody such as, for example, CGRP binding activity and/or antagonist activity, and comprises or consists of one or more of: (i) a light chain, (ii) a heavy chain, (iii) a fragment containing one or more variable regions from a light chain and/or a heavy chain, and (iv) one or more CDRs from a light chain and/or a heavy chain of the antibody G1.

In some embodiments, the anti-CGRP antagonist antibody comprises a light chain variable region (LCVR) comprising a peptide with a sequence selected from the group consisting of SEQ ID NOs: 28-32 and/or a heavy chain variable region (HCVR) comprising a peptide with a sequence selected from the group consisting of SEQ ID NOs: 34-38 of patent application WO2007/076336.

Further preferably, the anti-CGRP antagonist antibody comprises an LCVR polypeptide of a SEQ ID NO as shown in Table 1 of patent application WO2007/076336 and further comprises a HCVR polypeptide of a SED ID NO as shown in Table 1 of patent application WO2007/076336.

According to a further embodiment of the invention, the anti-CGRP antagonist antibody used comprises a light chain CDR (CDRL) selected from the group consisting of SEQ ID NOs: 8-13 and/or a heavy chain CDR (CDRH) selected from the group consisting of SEQ ID NOs: 14-22 of patent application WO2007/076336.

Methods of making and isolating the anti-CGRP antagonist antibodies of application WO2007/076336 and data demonstrating the CGRP binding and antagonist characterisation of the same are described in application WO2007/076336.

In some embodiments, the anti-CGRP antagonist antibody for use in the present invention comprises a VH domain that is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97% at least about 98%, at least about 99% or 100% identical in amino acid sequence to SEQ ID NO: 1 or SEQ ID NO: 19 presented herein.

In some embodiments, the anti-CGRP antagonist antibody comprises a VL domain that is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97% at least about 98%, at least about 99% or 100% identical in amino acid sequence to SEQ ID NO: 2 or SEQ ID NO: 20 presented herein.

In some embodiments, the anti-CGRP antagonist antibody comprises a VH domain and a VL domain that are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97% at least about 98%, at least about 99% or 100% identical in amino acid sequence to SEQ ID NO: 1 and 2 respectively or SEQ ID NO: 19 and 20 presented herein, respectively.

In some embodiments, the anti-CGRP antagonist antibody comprises a VH domain that is at least 90% identical in amino acid sequence to SEQ ID NO: 1 and a VL domain that is at least 90% identical in amino acid sequence to SEQ ID NO: 2 presented herein.

Alternatively, the anti-CGRP antagonist antibody can comprise a VH domain that is at least 90% identical in amino acid sequence to SEQ ID NO: 19 and a VL domain that is at least 90% identical in amino acid sequence to SEQ ID NO: 20 presented herein.

In some embodiments, the anti-CGRP antagonist antibody comprises at least one CDR selected from the group consisting of: (a). CDR H1 as set forth in SEQ ID NO: 3, 21, 33, 34, 36 or 37; (b). CDR H2 as set forth in SEQ ID NO: 4, 22, 35 or 38; (c). CDR H3 as set forth in SEQ ID NO: 5 or 23; (d). CDR L1 as set forth in SEQ ID NO: 6 or 24; (e) CDR L2 as set forth in SEQ ID NO: 7 or 25; (f). CDR L3 as set forth in SEQ ID NO: 8 or 26; and (g). variants of CDR L1, CDR L2 and CDR H2 as shown in Table 6 of WO2007/054809.

In some embodiments, the anti-CGRP antagonist antibody heavy chain constant region may be from any types of constant region, such as IgG, IgM, IgD, IgA, and IgE; and any isotypes, such as IgG1, IgG2, IgG3, and IgG4.

In some embodiments, the anti-CGRP antagonist antibody comprises a heavy chain produced by the expression vector with ATCC Accession No. PTA-6867. Further preferably the anti-CGRP antagonist antibody comprises a light chain produced by the expression vector with ATCC Accession No. PTA-6866. In some embodiments, the anti-CGRP antagonist antibody comprises the antibody G1 heavy chain full antibody amino acid sequence (including modified IgG2 as described herein) shown in SEQ ID NO: 11, with or without the C-terminal lysine. The anti-CGRP antagonist antibody also includes an antibody lacking a terminal lysine on the heavy chain, as this is normally lost in a proportion of antibodies during manufacture. In some embodiments, the anti-CGRP antagonist antibody comprises the antibody G1 light chain full antibody amino acid sequence shown in SEQ ID NO: 12. In some embodiments, the anti-CGRP antagonist antibody comprises the antibody G2 heavy chain full antibody amino acid sequence shown in SEQ ID NO: 29. In some embodiments, the anti-CGRP antagonist antibody comprises the antibody G2 light chain full antibody amino acid sequence shown in SEQ ID NO: 30. In some embodiments, the anti-CGRP antagonist antibody is produced by the expression vectors with ATCC Accession Nos. PTA-6867 and PTA-6866.

In some embodiments, the anti-CGRP antagonist antibody for use in the present invention is antibody G1 or antibody G2 defined herein. In preferred embodiments, the anti-CGRP antagonist antibody for use in the present invention is antibody G1, or an antigen binding fragment thereof.

According to further embodiments of the invention, the anti-CGRP antagonist antibody comprises a modified constant region as for example described in WO2007/054809. Preferably, the modified constant region is immunologically inert, including partially immunologically inert, such that it does not trigger complement mediated lysis, does not stimulate antibody-dependent cell mediated cytotoxicity (ADCC), does not activate microglia. Preferably, the modified constant region is reduced in one or more of these activities. Most preferably, the constant region is modified as described in Eur. J. Immunol., 1999, 29:2613-2624; PCT Application No. PCT/GB99/01441; and/or UK Patent Application No. 9809951.8. In some embodiments, the anti-CGRP antagonist antibody comprises a human heavy chain IgG2 constant region comprising the following mutations: A330, P331 to S330, S331 (amino acid numbering with reference to the wildtype IgG2 sequence). Eur. J. Immunol., 1999, 29:2613-2624.

Methods of making and isolating the anti-CGRP antagonist antibodies of application WO2007/054809 and data demonstrating the CGRP binding and antagonist characterisation of the same are described in application WO2007/054809. Sequences of SEQ ID NO: 1 to 14 of said application are provided herein as SEQ ID NO: 1 to 14, respectively.

Dosage and Administration

In some embodiments, the anti-CGRP antagonist antibody is peripherally administered between, for example, about once to about 7 times per week, further preferably between about once to about four times per month, further preferably between about once to about six times per 6 month period, further preferably about once to about twelve times per year. Preferably, the anti-CGRP antagonist antibody is peripherally administered in a period selected from: about once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly. According to preferred embodiments, the anti-CGRP antagonist antibody is administered via a route selected from one or more of: orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

According to a further embodiment of the present invention, the medicament is prepared for peripheral administration between about once to about 7 times per week, further preferably between about once to about four times per month, further preferably between about once to about six times per 6 month period, further preferably about once to about twelve times per year. Preferably, the medicament is prepared to be peripherally administered in a period selected from: about once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly. According to preferred embodiments, the medicament is prepared to be peripherally administered via a route selected from one or more of: orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

According to a further embodiment of the present invention, an antibody concentration of between about 0.1 to about 200 mg/ml; preferably at any one of about 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or 200 mg/ml+/−10% error, most preferably at about 50 mg/ml.

According to a further embodiment of the present invention the medicament is prepared for peripheral administration with an antibody concentration of between 0.1 to 200 mg/kg of body weight; preferably at any one of about 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or 200 mg/kg of body weight+/−10% error, most preferably at about 10 mg/kg.

According to a preferred embodiment of the present invention the anti-CGRP antagonist antibody has a half life in-vivo of more than any one of about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 days+/−1 day, further preferably more than any one of about 7, 8, 9, 10, 11, or 12 months.

Preferably, the anti-CGRP antagonist antibody has a half life in-vivo of more than 6 days.

According to a further preferred embodiment of the present invention, the medicament and/or the anti-CGRP antagonist antibody does not produce effects of central nervous system and/or cognitive impairment. Preferably the medicament and/or the anti-CGRP antagonist antibody does not induce any one or more of the following: amnesia, confusion, depersonalization, hypesthesia, abnormal thinking, trismus, vertigo, akathisia, apathy, ataxia, circumoral paresthesia, CNS stimulation, emotional lability, euphoria, hallucinations, hostility, hyperesthesia, hyperkinesia, hypotonia, incoordination, libido increase, manic reaction, myoclonus, neuralgia, neuropathy, psychosis, seizure, abnormal speech, stupor, suicidal ideation; dizziness, somnolence, Insomnia, anxiety, tremor, depression or paresthesia. Most preferably the medicament and/or the anti-CGRP antagonist antibody does not induce impairment of motor coordination or attention.

According to a further embodiment of the present invention, the medicament and/or the anti-CGRP antagonist antibody does not produce respiratory, liver renal or gastro-intestinal impairment.

According to a further embodiment of the present invention, the medicament and/or the anti-CGRP antagonist antibody does not produce effects of physical and/or psychological dependence. Preferably the medicament and/or the anti-CGRP antagonist antibody does not demonstrate affinity for opiate, benzodiazepine, phencyclidine (PCP), or N-methyl-D-aspartic acid (NMDA) receptors, or CNS stimulant, or produce any sedating or euphoric effect.

In some embodiments, the anti-CGRP antagonist antibody, on administration, ameliorates, controls, reduces incidence of, or delays the development or progression of central pain sensation.

In other embodiments, the effect of the anti-CGRP antagonist antibody is equal and/or superior to the effects of NSAIDS and/or opiates in the same models of visceral pain. In one embodiment, the anti-CGRP antagonist antibody is effective in treating refractory pain populations.

According to further embodiments of the present invention, there is provided the use or method according to any other aspect of the invention wherein the anti-CGRP antagonist antibody is administered separately, sequentially or simultaneously in combination with one or more further pharmacologically active compounds or agents, preferably compounds or agents useful for treating visceral pain. Preferably, the additional agent(s) is/are selected from one or more of:

(i) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof;

(iii) a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;

(iv) a benzodiazepine having a sedative action, e.g. chlordiazepoxide, clorazepate, diazepam, flurazepam, lorazepam, oxazepam, temazepam or triazolam or a pharmaceutically acceptable salt thereof;

(v) an $H_1$ antagonist having a sedative action, e.g. diphenhydramine, pyrilamine, promethazine, chlorpheniramine or chlorocyclizine or a pharmaceutically acceptable salt thereof;

(vi) a sedative such as glutethimide, meprobamate, methaqualone or dichloralphenazone or a pharmaceutically acceptable salt thereof;

(vii) a skeletal muscle relaxant, e.g. baclofen, carisoprodol, chlorzoxazone, cyclobenzaprine, methocarbamol or orphrenadine or a pharmaceutically acceptable salt thereof;

(viii) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;

(ix) an alpha-adrenergic, e.g. doxazosin, tamsulosin, clonidine or 4-amino-6,7-dimethoxy-2-(5-methanesulfonamido-1,2,3,4-tetrahydroisoquinol-2-yl)-5-(2-pyridyl) quinazoline;

(x) a tricyclic antidepressant, e.g. desipramine, imipramine, amytriptiline or nortriptiline;

(xi) an anticonvulsant, e.g. carbamazepine or valproate;

(xii) a tachykinin (NK) antagonist, particularly an NK-3, NK-2 or NK-1 antagonist, e.g. ($\alpha$R,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S, 3S);

(xiii) a muscarinic antagonist, e.g oxybutin, tolterodine, propiverine, tropsium chloride or darifenacin;

(xiv) a COX-2 inhibitor, e.g. celecoxib, rofecoxib or valdecoxib;

(xv) a non-selective COX inhibitor (preferably with G1 protection), e.g. nitroflurbiprofen (HCT-1026);

(xvi) a coal-tar analgesic, in particular paracetamol;

(xvii) a neuroleptic such as droperidol;

(xviii) a vanilloid receptor agonist (e.g. resinferatoxin) or antagonist (e.g. capsazepine);

(xix) a beta-adrenergic such as propranolol;

(xx) a local anaesthetic, such as mexiletine;

(xxi) a corticosteriod, such as dexamethasone;

(xxii) a serotonin receptor agonist or antagonist;

(xxiii) a cholinergic (nicotinic) analgesic;

(xxiv) tramadol;

(xxv) a PDEV inhibitor, such as sildenafil, vardenafil or taladafil;

(xxvi) an alpha-2-delta ligand such as gabapentin or pregabalin;

(xxvii) a canabinoid; and (xxviii) an antidepressant, such as amitriptyline (Elavil®), trazodone (Desyrel®), and imipramine (Tofranil®) or anticonvulsants such as phenyloin (Dilantin®) or carbamazepine (Tegretol®).

According to a further aspect of the present invention there is provided a pharmaceutical composition for the prevention and/or treatment of visceral pain and/or symptoms of visceral pain or for ameliorating, controlling, reducing incidence of, or delaying the development or progression of visceral pain and/or symptoms of visceral pain in an individual, comprising an anti-CGRP antagonist antibody and a pharmaceutically acceptable carrier and/or an excipient, wherein the composition is prepared to be peripherally administered.

Kits

According to a further aspect of the present invention there is provided a kit comprising a pharmaceutical composition as defined above, and instructions for the peripheral administration of an effective amount of said pharmaceutical composition to an individual for the prevention and/or treatment of visceral pain and/or symptoms of visceral pain or for ameliorating, controlling, reducing incidence of, or delaying the development or progression of visceral pain and/or symptoms of visceral pain.

The kit may include one or more containers containing an anti-CGRP antagonist antibody or polypeptide described herein and instructions for use in accordance with any of the methods and uses of the invention. The kit may further comprise a description of selecting an individual suitable for treatment based on identifying whether that individual has visceral pain or is at risk of having visceral pain. The instructions for the peripheral administration of the pharmaceutical composition may include information as to dosage, dosing schedule and routes of administration for the intended treatment.

Preferred features of each aspect of the invention apply equally to each other aspect mutatis mutandis.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Visceral Pain Model

This Example illustrates the effect of anti-CGRP antagonist antibody treatment in a visceral pain model.

Patients with IBS have been shown to have a lower visceral sensory threshold to colorectal distension and that this is highly correlated to the visceral pain symptoms (Delafoy et al, 2006). Colorectal distension after TNBS-induced colitis in rats is an animal model that has been used by many researchers to explore the mechanisms of visceral hypersensitivity (Gay et al, 2006, Delafoy et al, 2006, Adam et al., 2006). In this Example, the rat TNBS colitis model was used to test the effect of a function-blocking antibody for CGRP. In the model, as in the human IBS studies, the visceral pain threshold is measured by response to balloon distension of the colon.

After overnight fasting, rats were anesthetized with ketamine (80 mg/ml)/xylazine (12 mg/ml) at a dosage of 1 ml/kg. An abdominal laparotomy was performed and a TNBS solution (50 mg at 1.5 ml/kg in 30% ethanol, "TNBS treatment group") or 30% ethanol solution ("sham group") was injected into the proximal colon 1 cm distal from ceacum. The sham group was used as a non-colitis control. On the fifth day following surgery, the TNBS treatment group was subdivided into two groups. One group received anti-CGRP antagonist monoclonal antibody 4901 (commercially available at Sigma (Missouri, US), product number C7113, clone #4901) at 10 mg/kg intravenously. The other group received vehicle (PBS, 0.01% tween 20) as a negative control.

The seventh day following surgery, after a second overnight fast, TNBS treated rats sustaining a weight loss of no greater than 11% were tested for visceral pain threshold with balloon distension. A 5 cm latex balloon attached to a catheter was inserted into the distal colon with the base of the balloon 5 cm from the anus. The catheter was fixed to the tail with tape to prevent balloon movement. After a 30-minute acclimation period the balloon was inflated sequentially from 5 mmHg to 80 mmHg in 30-second intervals. Balloon distension was halted at the threshold pressure required to elicit a stereotypical rodent visceral pain posture known as the alpha position (repeated waves of contraction of oblique musculature with inward turning of the hindpaw) and this was recorded as the visceral pain threshold.

Rats undergoing sham procedure had a threshold of 36.8+/−2.6 (N=5, mean+/−se) on day 7 post surgery (FIG. 1A). TNBS treated rats that received antibody 4901 (10 mg/kg) on day 5 had a threshold of 32.3+/−4.1 (N=9) on day 7 and were statistically significantly different (one-way ANOVA plus Dunnet's multiple comparison post-test) from the day 7 threshold of TNBS treated rats that received vehicle on day 5 (21.0+/−3.0, N=10) (FIG. 1A). The effect of 4901 was comparable to CGRP receptor antagonist CGRP 8-37 (FIG. 1B). This result demonstrated that an anti-CGRP antagonist antibody was effective in significantly shifting the visceral pain threshold towards the sham threshold, i.e., reversing pain, in a visceral pain model.

Example 2

Interaction Analysis and Binding Assay

Interaction analysis was conducted at 25° C. and at 37° C. on a Biacore 3000™ system equipped with streptavidin-coated (SA) sensor chips (Biacore AB, Uppsala, Sweden) using standard Biacore running buffers (HBS-P or HBS-EP). N-LC-biotinylated human and rat α- and β-CGRPs were captured on individual flow cells at low levels (typically 100 response units) to provide the reaction surfaces, while an unmodified flow cell served as a reference channel. Purified Fab fragments of antibodies G1 and G2 were generated. Typically, Fabs were prepared as a two-fold serial dilution using 0.5 μM as the top concentration and injected for 1-min at 100 μl/min allowing up to two hours for the dissociation time. Surfaces were regenerated with a mixture of 50% v/v ethanol+25 mM NaOH for G1 Fab and 2:1 v/v Pierce Gentle Elution Buffer/4M NaCl for G2 Fab. Fab injections were duplicated to demonstrate that the assay was reproducible. The binding responses were double-referenced and fit globally to a simple model using BiaEvaluation v. 4.0 software. Affinities were deduced from the quotient of the kinetic rate constants ($K_D = k_{off}/k_{on}$).

The results for antibody G1 are expressed in Table 1 below. Antibody G1 binds human α- and β-CGRP with similar and tight affinities ($K_D$=163 and 155 μM, respectively when analyzed side-by-side on the same chip at 37° C., allowing a 20-min dissociation time). Human and cynomolgus monkey have identical sequences; therefore, the human data also apply to cynomolgus. G1 also binds rat CGRPs but discriminates between α- and β-isoforms ($K_D$=2.57 nM and <150 μM, respectively, at 37° C.).

TABLE 1

$K_D$ of G1 antibody measured at 25° C. and 37° C. against human and rat CGRPs.

| N-biotin-CGRP on chip | Temp (° C.) | $k_{on}$ (1/Ms) | $k_{off}$ (1/s) | $T_{1/2}$ (h) | $K_D$ (nM) |
|---|---|---|---|---|---|
| α-human/cyno | 25 | 1.86 × 10⁵ | 7.80 × 10⁻⁶ | 24.68 | 0.042 |
| α-human/cyno | 37 | 5.87 × 10⁵ | 3.63 × 10⁻⁵ | 5.30 | 0.063 |
| β-human/cyno | 37 | 4.51 × 10⁵ | <6.98 × 10⁻⁵ | 2.76 | <0.155 |
| α-rat | 25 | 5.08 × 10⁴ | 6.18 × 10⁻⁵ | 3.12 | 1.22 |
| α-rat | 37 | 1.55 × 10⁵ | 3.99 × 10⁻⁴ | 0.48 | 2.57 |
| β-rat | 37 | 5.16 × 10⁵ | <7.85 × 10⁻⁵ | 2.45 | <0.152 |

The dissociation of G1 Fab from α-human, β-human, and β-human-CGRPs occurs very slowly. As such, the offrate ($k_{off}$) cannot be measured accurately unless the dissociation phase is monitored for a very long time. As a general rule-of-thumb, the binding response decays at least 5% over the allowed dissociation time for the report of an accurate offrate. However, monitoring long dissociation times on the Biacore is hindered by baseline drift, which is particularly challenging when working at the low surface capacities required for kinetic analyses. In this study, the dissociation phase was followed for two hours over the α-CGRPs but only 20 mins over the β-CGRPs. As a result, the offrates for β-CGRPs cannot be resolved as accurately as those for α-CGRPs. However, when assayed side-by-side on the same chip under identical conditions and using a 20-min dissociation time, G1 had virtually the same binding kinetics for α-human/cyno, β-human/cyno, and β-rat CGRPs ($K_D$=150 μM at 37° C.).

The results for antibody G2 are expressed in Table 2. Antibody G2 binds α-rat CGRP with tighter affinity ($K_D$=0.9 nM at 25° C.) than the α- and β-human CGRPs ($K_D$=19 nM and 20 nM respectively at 25° C.). G2 binding β-rat CGRP was not examined in this assay format, but showed comparable binding characteristics to α- and β-human CGRPs in a reverse orientation assay format (data not shown).

TABLE 2

$K_D$ of G2 antibody measured at 25° C. and 37° C. against human and rat CGRPs.

| N-biotin CGRP on chip | Temp (° C.) | $k_{on}$ (1/Ms) | $k_{off}$ (1/s) | $T_{1/2}$ (min) | $K_D$ (nM) |
|---|---|---|---|---|---|
| α-rat | 25 | 2.31 × 10⁵ | 2.14 × 10⁻⁴ | 53.98 | 0.9 |
| α-rat | 37 | 5.0 × 10⁵ | 1.7 × 10⁻³ | 6.80 | 3.4 |
| α-human | 25 | 6.03 × 10⁴ | 1.15 × 10⁻³ | 10.05 | 19.1 |
| α-human | 37 | 9.3 × 10⁴ | 3.9 × 10⁻³ | 2.96 | 41.9 |
| β-human | 25 | 8.14 × 10⁴ | 1.62 × 10⁻³ | 7.13 | 19.9 |

A binding assay was performed to measure the $IC_{50}$ of anti-CGRP G1 antibody in blocking human α-CGRP from binding to the CGRP1-receptor. Membranes (25 μg) from SK-N-MC cells were incubated for 90 minutes at 25° C. in incubation buffer (50 mM Tris-HCl, pH 7.4, 5 mM $MgCl_2$, 0.1% BSA) containing 10 μM $^{125}$I-human α-CGRP and varying concentrations of anti-CGRP antibody (0.015 nM-33 nM) in a total volume of 1 ml. Incubation was terminated by filtration through a glass microfiber filter (GF/B, 1 μm) which had been blocked with 0.5% polyethylenimine. The protein-bound radioactivity was determined in a gamma counter. Dose response curves were plotted and K values were determined using the equation: $K_i=IC_{50}/(1+([ligand]/K_D))$; where the equilibrium dissociation constant $K_D$=8 pM for human α-CGRP to CGRP1-receptor as present in SK-N-MC cells. The reported $IC_{50}$ value (in terms of IgG molecules) was converted to binding sites (by multiplying it by 2 to allow for the fact that the Biacore was analysis of Fab fragments) so that it could be compared with the affinities ($K_D$) determined by Biacore. The $IC_{50}$ observed (1.8 nM) was 23-fold higher than the $K_D$ observed by Biacore (42 pM) at equivalent temperature. This mismatch reflects a possible lack of sensitivity of the binding assay.

Example 3

Visceral Pain Model

This Example illustrates the effect of anti-CGRP antagonist antibody treatment in a visceral pain model.

In this Example, the rat interstitial cystitis model was used to test the effect of a function-blocking antibody for CGRP. In the model, visceral hypersensitivity was measured by bladder motility in response to turpentine irritation of the bladder.

Female rats were maintained under urethane anesthesia during cystometry and were not allowed to recover. Body temperature was maintained at 37° C. by the use of a rectal probe, thermostatically connected to a temperature controlled heating pad. One group of rats (n=7) received anti-CGRP antagonist monoclonal antibody 4901 (commercially available at Sigma (Missouri, US), product number C7113, clone #4901) at 10 mg/kg intravenously. Another group (n=7) received vehicle (PBS, 0.01% tween 20) as a negative control.

Twenty-four hours after dosing with 4901 or vehicle, rats were anesthetized, and the bladder was catheterized transurethrally with PE50 tubing (1 mm OD) to allow 0.06 ml/min filling (using a syringe pump) of the bladder with normal saline. The tubing has a T joint proximal to the bladder to allow monitoring of the bladder pressure with a pressure transducer. Pressure and contractions were monitored during a 14-minute interval (0.84 ml total volume) to determine bladder motility. After establishing a baseline cystometrogram, bladder irritation was created by infusing 0.5 ml of 50% turpentine oil for 1 hour. The bladder was then drained and subsequent tests of bladder motility were performed immediately post (1 h), 3 h and 5 h post-turpentine.

Rats that received antibody 4901 (10 mg/kg) 24 hours prior to the cystometrogram procedure had fewer bladder contractions at all time points measured compared to rats that received vehicle (FIG. 2). This result demonstrated that an anti-CGRP antagonist antibody was effective in reducing bladder motility in response to turpentine irritation, i.e., reversing pain, in a visceral pain model.

Deposit of Biological Material

The following materials have been deposited with the American Type Culture Collection, 10801 University Boulevard, Manassas, Va. 20110-2209, USA (ATCC):

| Material | Antibody No. | ATCC Accession No. | Date of Deposit |
|---|---|---|---|
| pDb.CGRP.hFcGI | G1 heavy chain | PTA-6867 | Jul. 15, 2005 |
| pEb.CGRP.hKGI | G1 light chain | PTA-6866 | Jul. 15, 2005 |

Vector pEb.CGRP.hKGI is a polynucleotide encoding the G1 light chain variable region and the light chain kappa constant region; and vector pDb.CGRP.hFcGI is a polynucleotide encoding the G1 heavy chain variable region and the heavy chain IgG2 constant region containing the following mutations: A330P331 to S330S331 (amino acid numbering with reference to the wildtype IgG2 sequence; see Eur. J. Immunol., 1999, 29:2613-2624).

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Rinat Neuroscience Corp. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Below are given antibody sequences useful for various embodiments disclosed herein.

```
Antibody sequences
Antibody G1 heavy chain variable region amino acid
sequence
                                            (SEQ ID NO: 1)
EVQLVESGGGLVQPGGSLRLSCAASGFTFSNYWISWVRQAPGKGLEWVAE

IRSESDASATHYAEAVKGRFTISRDNAKNSLYLQMNSLRAEDTAVYYCLA

YFDYGLAIQNYWGQGTLVTVSS

Antibody G1 light chain variable region amino acid
sequence
                                            (SEQ ID NO: 2)
EIVLTQSPATLSLSPGERATLSCKASKRVTTYVSWYQQKPGQAPRLLIYG

ASNRYLGIPARFSGSGSGTDFTLTISSLEPEDFAVYYCSQSYNYPYTFGQ

GTKLEIK

Antibody G1 CDR H1 (extended CDR)
                                            (SEQ ID NO: 3)
GFTFSNYWIS Antibody G1 CDR H2 (extended CDR, same as
Kabat CDR)
                                            (SEQ ID NO: 4)
EIRSESDASATHYAEAVKG Antibody G1 CDR H3
                                            (SEQ ID NO: 5)
YFDYGLAIQNY Antibody G1 CDR L1
                                            (SEQ ID NO: 6)
KASKRVTTYVS Antibody G1 CDR L2
                                            (SEQ ID NO: 7)
GASNRYL Antibody G1 CDR L3
                                            (SEQ ID NO: 8)
SQSYNYPYT
```

Antibody G1 heavy chain variable region nucleotide
sequence
(SEQ ID NO: 9)
GAAGTTCAGCTGGTTGAATCCGGTGGTGGTCTGGTTCAGCCAGGTGGTTC

CCTGCGTCTGTCCTGCGCTGCTTCCGGTTTCACCTTCTCCAACTACTGGA

TCTCCTGGGTTCGTCAGGCTCCTGGTAAAGGTCTGGAATGGGTTGCTGAA

ATCCGTTCCGAATCCGACGCGTCCGCTACCCATTACGCTGAAGCTGTTAA

AGGTCGTTTCACCATCTCCCGTGACAACGCTAAGAACTCCCTGTACCTGC

AGATGAACTCCCTGCGTGCTGAAGACACCGCTGTTTACTACTGCCTGGCT

TACTTTGACTACGGTCTGGCTATCCAGAACTACTGGGGTCAGGGTACCCT

GGTTACCGTTTCCTCC

Antibody G1 light chain variable region nucleotide
sequence
(SEQ ID NO: 10)
GAAATCGTTCTGACCCAGTCCCCGGCTACCCTGTCCCTGTCCCAGGTGA

ACGTGCTACCCTGTCCTGCAAAGCTTCCAAACGGGTTACCACCTACGTTT

CCTGGTACCAGCAGAAACCCGGTCAGGCTCCTCGTCTGCTGATCTACGGT

GCTTCCAACCGTTACCTCGGTATCCCAGCTCGTTTCTCCGGTTCCGGTTC

CGGTACCGACTTCACCCTGACCATCTCCTCCCTGGAACCCGAAGACCTTC

GTGTTTACTACTGCAGTCAGTCCTACAACTACCCCTACACCTTCGGTCAG

GGTACCAAACTGGAAATCAAA

Antibody G1 heavy chain full antibody amino acid
sequence (including modified IgG2 as described
herein)
(SEQ ID NO: 11)
EVQLVESGGGLVQPGGSLRLSCAASGFTFSNYWISWVRQAPGKGLEWVAE

IRSESDASATHYAEAVKGRFTISRDNAKNSLYLQMNSLRAEDTAVYYCLA

YFDYGLAIQNYWGQGTLVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNST

FRVVSVLTVVHQDWLNGKEYKCKVSNKGLPSSIEKTISKTKGQPREPQVY

TLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGK

Antibody G1 light chain full antibody amino acid
sequence
(SEQ ID NO: 12)
EIVLTQSPATLSLSPGERATLSCKASKRVTTYVSWYQQKPGQAPRLLIYG

ASNRYLGIPARFSGSGSGTDFTLTISSLEPEDFAVYYCSQSYNYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Antibody G1 heavy chain full antibody nucleotide
sequence (including modified IgG2 as described
herein)
(SEQ ID NO: 13)
GAAGTTCAGCTGGTTGAATCCGGTGGTGGTCTGGTTCAGCCAGGTGGTTC

CCTGCGTCTGTCCTGCGCTGCTTCCGGTTTCACCTTCTCCAACTACTGGA

TCTCCTGGGTTCGTCAGGCTCCTGGTAAAGGTCTGGAATGGGTTGCTGAA

ATCCGTTCCGAATCCGACGCGTCCGCTACCCATTACGCTGAAGCTGTTAA

AGGTCGTTTCACCATCTCCCGTGACAACGCTAAGAACTCCCTGTACCTGC

AGATGAACTCCCTGCGTGCTGAAGACACCGCTGTTTACTACTGCCTGGCT

TACTTTGACTACGGTCTGGCTATCCAGAACTACTGGGGTCAGGGTACCCT

GGTTACCGTTTCCTCCGCCTCCACCAAGGGCCCATCTGTCTTCCCACTGG

CCCCATGCTCCCGCAGCACCTCCGAGAGCACAGCCGCCCTGGGCTGCCTG

GTCAAGGACTACTTCCCAGAACCTGTGACCGTGTCCTGGAACTCTGGCGC

TCTGACCAGCGGCGTGCACACCTTCCCAGCTGTCCTGCAGTCCTCAGGTC

TCTACTCCCTCAGCAGCGTGGTGACCGTGCCATCCAGCAACTTCGGCACC

CAGACCTACACCTGCAACGTAGATCACAAGCCAAGCAACACCAAGGTCGA

CAAGACCGTGGAGAGAAAGTGTTGTGTGGAGTGTCCACCTTGTCCAGCCC

CTCCAGTGGCCGGACCATCCGTGTTCCTGTTCCCTCCAAAGCCAAAGGAC

ACCCTGATGATCTCCAGAACCCCAGAGGTGACCTGTGTGGTGGTGGACGT

GTCCCACGAGGACCCAGAGGTGCAGTTCAACTGGTATGTGGACGGAGTGG

AGGTGCACAACGCCAAGACCAAGCCAAGAGAGGAGCAGTTCAACTCCACC

TTCAGAGTGGTGAGCGTGCTGACCGTGGTGCACCAGGACTGGCTGAACGG

AAAGGAGTATAAGTGTAAGGTGTCCAACAAGGGACTGCCATCCAGCATCG

AGAAGACCATCTCCAAGACCAAGGGACAGCCAAGAGAGCCACAGGTGTAT

ACCCTGCCCCCATCCAGAGAGGAGATGACCAAGAACCAGGTGTCCCTGAC

CTGTCTGGTGAAGGGATTCTATCCATCCGACATCGCCGTGGAGTGGGAGT

CCAACGGACAGCCAGAGAACAACTATAGACCACCCCTCCAATGCTGGACT

CCGACGGATCCTTCTTCCTGTATTCCAAGCTGACCGTGGACAAGTCCAGA

TGGCAGCAGGGAAACGTGTTCTCTTGTTCCGTGATGCACGAGGCCCTGCA

CAACCACTATACCCAGAAGAGCCTGTCCCTGTCTCCAGGAAAGTAA

Antibody G1 light chain full antibody nucleotide
sequence
(SEQ ID NO: 14)
GAAATCGTTCTGACCCAGTCCCCGGCTACCCTGTCCCTGTCCCAGGTGA

ACGTGCTACCCTGTCCTGCAAAGCTTCCAAACGGGTTACCACCTACGTTT

CCTGGTACCAGCAGAAACCCGGTCAGGCTCCTCGTCTGCTGATCTACGGT

GCTTCCAACCGTTACCTCGGTATCCCAGCTCGTTTCTCCGGTTCCGGTTC

CGGTACCGACTTCACCCTGACCATCTCCTCCCTGGAACCCGAAGACTTCG

CTGTTTACTACTGCAGTCAGTCCTACAACTACCCCTACACCTTCGGTCAG

GGTACCAAACTGGAAATCAAACGCACTGTGGCTGCACCATCTGTCTTCAT

CTTCCCTCCATCTGATGAGCAGTTGAAATCCGGAACTGCCTCTGTTGTGT

GCCTGCTGAATAACTTCTATCCGCGCGAGGCCAAAGTACAGTGGAAGGTG

GATAACGCCCTCCAATCCGGTAACTCCCAGGAGAGTGTCACAGAGCAGGA

CAGCAAGGACAGCACCTACAGCCTCAGCAGCACCCTGACCCTGAGCAAAG

CAGACTACGAGAAACACAAAGTCTACGCCTGCGAAGTCACCCATCAGGGC

CTGAGTTCTCCAGTCACAAAGAGCTTCAACCGCGGTGAGTGCTAA

Amino acid sequence comparison of human and rat CGRP (human α-CGRP (SEQ ID NO: 15); human (β-CGRP (SEQ ID NO: 16); rat α-CGRP (SEQ ID NO: 17); and rat (β-CGRP (SEQ ID NO: 18)):

(SEQ ID NO: 15)
NH₂-ACDTATCVTHRLAGLLSRSGGVVKNNFVPTNVGSKAF-CONH₂

(SEQ ID NO: 16)
NH₂-ACNTATCVTHRLAGLLSRSGGMVKSNFVPTNVGSKAF-CONH₂

(SEQ ID NO: 17)
NH₂-SCNTATCVTHRLAGLLSRSGGVVKDNFVPTNVGSEAF-CONH₂

(SEQ ID NO: 18)
NH₂-SCNTATCVTHRLAGLLSRSGGVVKDNFVPTNVGSKAF-CONH₂

Antibody G2 heavy chain variable region amino acid sequence
(SEQ ID NO: 19)
EVQLQQSGPELVKPGASVKMSCKASGYTFTSSVMHWVKQKPGQGLEWIGY
INPYNDGTKYNEKFKGKATLTSDKSSSTAYMELSSLTSEDSAVYYCAKGG
NDGYWGQGTTLTVSS Antibody G2 light chain variable region amino acid sequence
(SEQ ID NO: 20)
EIVLTQSPTTMAASPGEKITITCSASSSISSIYLHWYQQKPGFSPKVLIY
RASNLASGVPARFSGSGSGTSYSLTIGTMEAEDVATYYCQQGSTIPFTFG
SGTKLEIK Antibody G2 CDR H1 (Kabat CDR)
(SEQ ID NO: 21)
SSVMH Antibody G2 CDR H2 (extended CDR)
(SEQ ID NO: 22)
YINPYNDGTKYNEKFKG Antibody G2 CDR H3
(SEQ ID NO: 23)
GGNDGY Antibody G2 CDR L1
(SEQ ID NO: 24)
SASSSISSIYLH Antibody G2 CDR L2
(SEQ ID NO: 25)
RASNLAS Antibody G2 CDR L3
(SEQ ID NO: 26)
QQGSTIPFT Antibody G2 heavy chain variable region nucleotide sequence
(SEQ ID NO: 27)
GAGGTCCAGCTGCAGCAGTCTGGACCTGAGCTGGTAAAGCCTGGGGCTTC
AGTGAAGATGTCCTGCAAGGCTTCTGGATACACATTCACTAGCTCTGTTA
TGCACTGGGTGAAGCAGAAGCCTGGGCAGGGCCTTGAGTGGATTGGATAT
ATTAATCCTTACAATGATGGTACTAAGTACAATGAAGAAGTTCAAAGGCAA
GGCCACACTGACTTCAGACAAATCCTCCAGCACAGCCTACATGGAACTCA
GCAGCCTGACCTCTGAGGACTCTGCGGTCTATTACTGTGCAAAAGGGGGT
AACGATGGCTACTGGGGCCAAGGCACTACTCTCACAGTCTCCTCA Antibody G2 light chain variable region nucleotide sequence
(SEQ ID NO: 28)
GAAATTGTGCTCACCCAGTCTCCAACCACCATGGCTGCATCTCCCGGGGA
GAAGATCACTATCACCTGTAGTGCCAGCTCAAGTATAAGTTCCATTTACT
TGCATTGGTATCAGCAGAAGCCAGGATTCTCCCCTAAAGTCTTGATTTAT
AGGGCATCCAATCTGGCTTCTGGAGTCCCAGCTCGCTTCAGTGGCAGTGG
GTCTGGGACCTCTTACTCTCTCACAATTGGCACCATGGAGGCTGAAGATG
TTGCCACTTACTACTGCCAGCAGGGTAGTACTATACCATTCACGTTCGGC
TCGGGGACAAAGTTGGAAATAAAA Antibody G2 heavy chain full antibody amino acid sequence (not including Fc domain)
(SEQ ID NO: 29)
EVQLQQSGPELVKPGASVKMSCKASGYTFTSSVMHWVKQKPGQGLEWIGY
INPYNDGTKYNEKFKGKATLTSDKSSSTAYMELSSLTSEDSAVYYCAKGG
NDGYWGQGTTLTVSSAKTTPPSVYPLAPGSAAQTNSMVTLGCLVKGYFPE
PVTVTWNSGSLSSGVHTFPAVLQSDLYTLSSSVTVPSSTWPSETVTCNVA
HPASSTKVDKKIVPRD Antibody G2 light chain full antibody amino acid sequence
(SEQ ID NO: 30)
EIVLTQSPTTMAASPGEKITITCSASSSISSIYLHWYQQKPGFSPKVLIY
RASNLASGVPARFSGSGSGTSYSLTIGTMEAEDVATYYCQQGSTIPFTFG
SGTKLEIKRADAAPTVSIFPPSSEQLTSGGASVVCFLNNFYPRDINVKWK
IDGSERQNGVLNSWTDQDSKDSTYSMSSTLTLTKDEYERHNSYTCEATHK
TSTSPIVKSFNRNEC Antibody G2 heavy chain full antibody nucleotide sequence (not including Fc domain)
(SEQ ID NO: 31)
GAGGTCCAGCTGCAGCAGTCTGGACCTGAGCTGGTAAAGCCTGGGGCTTC
AGTGAAGATGTCCTGCAAGGCTTCTGGATACACATTCACTAGCTCTGTTA
TGCACTGGGTGAAGCAGAAGCCTGGGCAGGGCCTTGAGTGGATTGGATAT
ATTAATCCTTACAATGATGGTACTAAGTACAATGAGAAGTTCAAAGGCAA
GGCCACACTGACTTCAGACAAATCCTCCAGCACAGCCTACATGGAACTCA
GCAGCCTGACCTCTGAGGACTCTGCGGTCTATTACTGTGCAAAAGGGGGT
AACGATGGCTACTGGGGCCAAGGCACTACTCTCACAGTCTCCTCAGCCAA
AACGACACCCCCATCTGTCTATCCACTGGCCCCTGGATCTGCTGCCCAAA
CTAACTCCATGGTGACCCTGGGATGCCTGGTCAAGGGCTATTTCCCTGAG
CCAGTGACAGTGACCTGGAACTCTGGATCCCTGTCCAGCGGTGTGCACAC
CTTCCCAGCTGTCCTGCAGTCTGACCTCTACACTCTGAGCAGCTCAGTGA
CTGTCCCCTCCAGCACCTGGCCCAGCGAGACCGTCACCTGCAACGTTGCC
CACCCGGCCAGCAGCACCAAGGTGGACAAGAAAATTGTGCCCAGGGAT Antibody G2 light chain full antibody nucleotide sequence
(SEQ ID NO: 32)
GAAATTGTGCTCACCCAGTCTCCAACCACCATGGCTGCATCTCCCGGGGA
GAAGATCACTATCACCTGTAGTGCCAGCTCAAGTATAAGTTCCATTTACT
TGCATTGGTATCAGCAGAAGCCAGGATTCTCCCCTAAAGTCTTGATTTAT -continued

```
AGGGCATCCAATCTGGCTTCTGGAGTCCCAGCTCGCTTCAGTGGCAGTGG

GTCTGGGACCTCTTACTCTCTCACAATTGGCACCATGGAGGCTGAAGATG

TTGCCACTTACTACTGCCAGCAGGGTAGTACTATACCATTCACGTTCGGC

TCGGGGACAAAGTTGGAAATAAAACGGGCTGATGCTGCACCAACTGTATC

CATCTTCCCACCATCCAGTGAGCAGTTAACATCTGGAGGTGCCTCAGTCG

TGTGCTTCTTGAACAACTTCTACCCCAGAGACATCAATGTCAAGTGGAAG

ATTGATGGCAGTGAACGACAAAATGGTGTCCTGAACAGTTGGACTGATCA

GGACAGCAAAGACAGCACCTACAGCATGAGCAGCACCCTCACATTGACCA

AGGACGAGTATGAACGACATAACAGCTATACCTGTGAGGCCACTCACAAG

ACATCAACTTCACCCATCGTCAAGAGCTTCAACAGGAATGAGTGTTAA
```

Antibody G1 CDR H1 (Chothia CDR)
(SEQ ID NO: 33)
GFTFSNY

Antibody G1 CDR H1 (Kabat CDR)
(SEQ ID NO: 34)
NYWIS

Antibody G1 CDR H2 (Chothia CDR)
(SEQ ID NO: 35)
RSESDASA

Antibody G2 CDR H1 (extended CDR)
(SEQ ID NO: 36)
GYTFTSSVMH

Antibody G2 CDR H1 (Chothia CDR)
(SEQ ID NO: 37)
GYTFTSS

Antibody G2 CDR H2 (Chothia CDR)
(SEQ ID NO: 38)
NPYNDG

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

The section headings used herein are for organizational purposes only and are not to be construed as limiting the described subject matter in any way. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of reducing incidence of or treating visceral pain and/or one or more symptoms of visceral pain in an individual, comprising administration of a therapeutically effective amount of an anti-CGRP antagonist antibody to the individual.

2. The method of claim 1, wherein the visceral pain is associated with a functional bowel disorder (FBD).

3. The method of claim 2, wherein the FBD is selected from the group consisting of gastro-esophageal reflux, dyspepsia, irritable bowel syndrome (IBS) and functional abdominal pain syndrome (FAPS).

4. The method of claim 1, wherein the visceral pain is associated with inflammatory bowel disease (IBD).

5. The method of claim 4, wherein the IBD is selected from the group consisting of Crohn's disease, ileitis and ulcerative colitis.

6. The method of claim 1, wherein the visceral pain is associated with renal colic, dysmenorrhea, cystitis, menstrual period, labor, menopause, prostatitis or pancreatitis.

7. The method of claim 6, wherein the visceral pain is associated with interstitial cystitis (IC).

8. The method of claim 1, wherein the anti-CGRP antagonist antibody binds CGRP with a $K_D$ of 50 nM or less (as measured by surface plasmon resonance at 37° C.);—and/or has a half life in-vivo of at least 7 days.

9. The method of claim 1, wherein the anti-CGRP antagonist antibody specifically binds to the C-terminal region of CGRP.

10. The method of claim 9, wherein the anti-CGRP antagonist antibody specifically recognizes the epitope defined by the sequence GSKAF (SEQ ID NO: 39).

11. The method of claim 1, wherein the anti-CGRP antibody comprises a VH domain having the amino acid sequence shown in SEQ ID NO: 1 or 19.

12. The method of claim 1, wherein the anti-CGRP antibody comprises a VL domain having the amino acid sequence shown in SEQ ID NO: 2 or 20.

13. The method of claim 1, wherein the anti-CGRP antibody comprises:
   (a) CDR H1 as set forth in SEQ ID NO: 3, 33, or 34; CDR H2 as set forth in SEQ ID NO: 4 or 35; CDR H3 as set forth in SEQ ID NO: 5; CDR L1 as set forth in SEQ ID NO: 6; CDR L2 as set forth in SEQ ID NO: 7; and CDR L3 as set forth in SEQ ID NO: 8;
   (b) CDR H1 as set forth in SEQ ID NO: 21, 36, or 37; CDR H2 as set forth in SEQ ID NO: 22 or 38; CDR H3 as set forth in SEQ ID NO: 23; CDR L1 as set forth in SEQ ID NO: 24; CDR L2 as set forth in SEQ ID NO: 25; and CDR L3 as set forth in SEQ ID NO: 26; or
   (c) a variant of an antibody according to (a) as shown in Table 6.

14. The method of claim 1, wherein the anti-CGRP antibody comprises a VH domain having the amino acid sequence shown in SEQ ID NO: 1 and a VL domain having the amino acid sequence shown in SEQ ID NO: 2.

15. The method of claim 1, wherein the anti-CGRP antibody is produced by the expression vectors with ATCC Accession Nos. PTA-6867 and/or PTA-6866.

16. The method of claim 1, wherein the anti-CGRP antibody comprises: the antibody G1 heavy chain full antibody amino acid sequence shown in SEQ ID NO: 11, with or without the C-terminal lysine; and the antibody G1 light chain full antibody amino acid sequence shown in SEQ ID NO: 12.

17. The method of claim 1, wherein the anti-CGRP antibody comprises: the antibody G2 heavy chain full antibody amino acid sequence shown in SEQ ID NO: 29; and the antibody G2 light chain full antibody amino acid sequence shown in SEQ ID NO: 30.

18. The method of claim 1, wherein the anti-CGRP antagonist antibody is a human or humanized antibody.

19. The method of claim 1, wherein the individual is human.

* * * * *

SEQUENCE LISTING

```
<160> NUMBER OF SEQ ID NOS: 39

<210> SEQ ID NO 1
<211> LENGTH: 122
<212> TYPE: PRT
<213> ORGANISM: Artificial sequence
<220> FEATURE:
<223> OTHER INFORMATION: Synthetic polypeptide, Antibody G1 heavy chain
      variable region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80
```

```
Leu Tyr Leu Gln Met Asn Ser Leu Arg Ala Glu Asp Thr Ala Val Tyr
            85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
            115                 120

<210> SEQ ID NO 2
<211> LENGTH: 107
<212> TYPE: PRT
<213> ORGANISM: Artificial sequence
<220> FEATURE:
<223> OTHER INFORMATION: Synthetic polypeptide, Antibody G1 light chain
      variable region

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
            35                  40                  45

Tyr Gly Ala Ser Asn Arg Tyr Leu Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
            85                  90                  95

Thr Phe Gly Gln Gly Thr Lys Leu Glu Ile Lys
            100                 105

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide, Antibody G1 CDR H1

<400> SEQUENCE: 3

Gly Phe Thr Phe Ser Asn Tyr Trp Ile Ser
1               5                   10

<210> SEQ ID NO 4
<211> LENGTH: 19
<212> TYPE: PRT
<213> ORGANISM: Artificial sequence
<220> FEATURE:
<223> OTHER INFORMATION: Synthetic polypeptide, Antibody G1 CDR H2

<400> SEQUENCE: 4

Glu Ile Arg Ser Glu Ser Asp Ala Ser Ala Thr His Tyr Ala Glu Ala
1               5                   10                  15

Val Lys Gly

<210> SEQ ID NO 5
<211> LENGTH: 11
<212> TYPE: PRT
<213> ORGANISM: Artificial sequence
<220> FEATURE:
<223> OTHER INFORMATION: Synthetic polypeptide, Antibody G1 CDR H3

<400> SEQUENCE: 5
```

Tyr Phe Asp Tyr Gly Leu Ala Ile Gln Asn Tyr
1               5                   10

<210> SEQ ID NO 6
<211> LENGTH: 11
<212> TYPE: PRT
<213> ORGANISM: Artificial sequence
<220> FEATURE:
<223> OTHER INFORMATION: Synthetic polypeptide, Antibody G1 CDR L1

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic polypeptide, Antibody G1 CDR L2

<400> SEQUENCE: 7

Gly Ala Ser Asn Arg Tyr Leu
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide, Antibody G1 CDR L3

<400> SEQUENCE: 8

Ser Gln Ser Tyr Asn Tyr Pro Tyr Thr
1               5

<210> SEQ ID NO 9
<211> LENGTH: 366
<212> TYPE: DNA
<213> ORGANISM: Artificial sequence
<220> FEATURE:
<223> OTHER INFORMATION: Synthetic oligonucleotide, Antibody G1 heavy
      chain variable region

<400> SEQUENCE: 9
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgtttacta ctgcctggct     300
tactttgact acggtctggc tatccagaac tactggggtc agggtaccct ggttaccgtt     360
tcctcc                                                                366

<210> SEQ ID NO 10
<211> LENGTH: 321
<212> TYPE: DNA
<213> ORGANISM: Artificial sequence
<220> FEATURE:
<223> OTHER INFORMATION: Synthetic oligonucleotide, Antibody G1 light
      chain variable region

<400> SEQUENCE: 10
gaaatcgttc tgacccagtc cccggctacc ctgtccctgt ccccaggtga acgtgctacc      60

-continued

```
ctgtcctgca aagcttccaa acgggttacc acctacgttt cctggtacca gcagaaaccc      120
ggtcaggctc ctcgtctgct gatctacggt gcttccaacc gttacctcgg tatcccagct      180
cgtttctccg gttccggttc cggtaccgac ttcaccctga ccatctcctc cctggaaccc      240
gaagacttcg ctgtttacta ctgcagtcag tcctacaact acccctacac cttcggtcag      300
ggtaccaaac tggaaatcaa a                                                321
```

<210> SEQ ID NO 11
<211> LENGTH: 448
<212> TYPE: PRT
<213> ORGANISM: Artificial sequence
<220> FEATURE:
<223> OTHER INFORMATION: Synthetic polypeptide, Antibody G1 heavy chain

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial sequence
<220> FEATURE:
<223> OTHER INFORMATION: Synthetic polypeptide, Antibody G1 light chain

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 1347
<212> TYPE: DNA
```

```
<213> ORGANISM: Artificial sequence
<220> FEATURE:
<223> OTHER INFORMATION: Synthetic oligonucleotide, Antibody G1 heavy
      chain

<400> SEQUENCE: 13
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgtttacta ctgcctggct     300
tactttgact acggtctggc tatccagaac tactggggtc agggtaccct ggttaccgtt     360
tcctccgcct ccaccaaggg cccatctgtc ttcccactgg ccccatgctc cgcagcacc     420 tccgagagca gccgcccct gggctgcctg gtcaaggact acttcccaga acctgtgacc     480
gtgtcctgga actctggcgc tctgaccagc ggcgtgcaca ccttcccagc tgtcctgcag     540
tcctcaggtc tctactccct cagcagcgtg gtgaccgtgc catccagcaa cttcggcacc     600
cagacctaca cctgcaacgt agatcacaag ccaagcaaca ccaaggtcga caagaccgtg     660
gagagaaagt gttgtgtgga gtgtccacct tgtccagccc ctccagtggc cggaccatcc     720
gtgttcctgt tccctccaaa gccaaaggac accctgatga tctccagaac cccagaggtg     780
acctgtgtgg tggtggacgt gtcccacgag gacccagagg tgcagttcaa ctggtatgtg     840
gacggagtgg aggtgcacaa cgccaagacc aagccaagag aggagcagtt caactccacc     900
ttcagagtgg tgagcgtgct gaccgtggtg caccaggact ggctgaacgg aaaggagtat     960
aagtgtaagg tgtccaacaa gggactgcca tccagcatcg agaagaccat ctccaagacc    1020
aagggacagc caagagagcc acaggtgtat accctgcccc catccagaga ggagatgacc    1080
aagaaccagg tgtccctgac ctgtctggtg aagggattct atccatccga catcgccgtg    1140
gagtgggagt ccaacggaca gccagagaac aactataaga ccaccccctcc aatgctggac    1200 tccgacggat ccttcttcct gtattccaag ctgaccgtgg acaagtccag atggcagcag    1260
ggaaacgtgt tctcttgttc cgtgatgcac gaggccctgc acaaccacta tacccagaag    1320
agcctgtccc tgtctccagg aaagtaa                                        1347

<210> SEQ ID NO 14
<211> LENGTH: 645
<212> TYPE: DNA
<213> ORGANISM: Artificial sequence
<220> FEATURE:
<223> OTHER INFORMATION: Synthetic oligonucleotide, Antibody G1 light
      chain

<400> SEQUENCE: 14
gaaatcgttc tgacccagtc cccggctacc ctgtccctgt cccaggtgac agtgctacc      60 ctgtcctgca aagcttccaa acgggttacc acctacgttt cctggtacca gcagaaaccc    120
ggtcaggctc tcgtctgct gatctacggt gcttccaacc gttacctcgg tatcccagct    180
cgtttctccg gttccggttc cggtaccgac ttcaccctga ccatctcctc cctggaaccc    240
gaagacttcg ctgtttacta ctgcagtcag tcctacaact ccccctacac cttcggtcag    300
ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg gataacgccc tccaatccgg taactcccag    480
```

```
gagagtgtca cagagcagga cagcaaggac agcacctaca gcctcagcag caccctgacc    540
ctgagcaaag cagactacga gaaacacaaa gtctacgcct gcgaagtcac ccatcagggc    600
ctgagttctc cagtcacaaa gagcttcaac cgcggtgagt gctaa                   645
```

```
<210> SEQ ID NO 15
<211> LENGTH: 37
<212> TYPE: PRT
<213> ORGANISM: Homo sapiens
<220> FEATURE:
<223> OTHER INFORMATION: Polypeptide, Alpha-CGRP

<400> SEQUENCE: 15

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 16
<211> LENGTH: 37
<212> TYPE: PRT
<213> ORGANISM: Homo sapiens
<220> FEATURE:
<223> OTHER INFORMATION: Polypeptide, Beta-CGRP

<400> SEQUENCE: 16

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 17
<211> LENGTH: 37
<212> TYPE: PRT
<213> ORGANISM: Rattus norvegicus
<220> FEATURE:
<223> OTHER INFORMATION: Polypeptide, Alpha-CGRP

<400> SEQUENCE: 17

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
        35

<210> SEQ ID NO 18
<211> LENGTH: 37
<212> TYPE: PRT
<213> ORGANISM: Rattus norvegicus
<220> FEATURE:
<223> OTHER INFORMATION: Polypeptide, Beta-CGRP

<400> SEQUENCE: 18

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
```

<210> SEQ ID NO 19
<211> LENGTH: 115
<212> TYPE: PRT
<213> ORGANISM: Artificial sequence
<220> FEATURE:
<223> OTHER INFORMATION: Synthetic polypeptide, Antibody G2 heavy chain
      variable region

<400> SEQUENCE: 19

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Asn Asp Gly Tyr Trp Gly Gln Gly Thr Thr Leu Thr
            100                 105                 110

Val Ser Ser
        115

<210> SEQ ID NO 20
<211> LENGTH: 108
<212> TYPE: PRT
<213> ORGANISM: Artificial sequence
<220> FEATURE:
<223> OTHER INFORMATION: Synthetic polypeptide, Antibody G2 light chain
      variable region

<400> SEQUENCE: 20

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Ile
            20                  25                  30

Tyr Leu His Trp Tyr Gln Gln Lys Pro Gly Phe Ser Pro Lys Val Leu
        35                  40                  45

Ile Tyr Arg Ala Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Phe Thr Phe Gly Ser Gly Thr Lys Leu Glu Ile Lys
            100                 105

<210> SEQ ID NO 21
<211> LENGTH: 5
<212> TYPE: PRT
<213> ORGANISM: Artificial sequence
<220> FEATURE:
<223> OTHER INFORMATION: Synthetic polypeptide, Antibody G2 Kabat CDR H1

<400> SEQUENCE: 21

Ser Ser Val Met His

```
<210> SEQ ID NO 22
<211> LENGTH: 17
<212> TYPE: PRT
<213> ORGANISM: Artificial sequence
<220> FEATURE:
<223> OTHER INFORMATION: Synthetic polypeptide, Antibody G2 CDR H2

<400> SEQUENCE: 22

Tyr Ile Asn Pro Tyr Asn Asp Gly Thr Lys Tyr Asn Glu Lys Phe Lys
1               5                   10                  15
Gly

<210> SEQ ID NO 23
<211> LENGTH: 6
<212> TYPE: PRT
<213> ORGANISM: Artificial sequence
<220> FEATURE:
<223> OTHER INFORMATION: Synthetic polypeptide, Antibody G2 CDR H3

<400> SEQUENCE: 23

Gly Gly Asn Asp Gly Tyr
1               5

<210> SEQ ID NO 24
<211> LENGTH: 12
<212> TYPE: PRT
<213> ORGANISM: Artificial sequence
<220> FEATURE:
<223> OTHER INFORMATION: Synthetic polypeptide, Antibody G2 CDR L1

<400> SEQUENCE: 24

Ser Ala Ser Ser Ser Ile Ser Ser Ile Tyr Leu His
1               5                   10

<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide, Antibody G2 CDR L2

<400> SEQUENCE: 25

Arg Ala Ser Asn Leu Ala Ser
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic polypeptide, Antibody G2 CDR L3

<400> SEQUENCE: 26

Gln Gln Gly Ser Thr Ile Pro Phe Thr
1               5

<210> SEQ ID NO 27
<211> LENGTH: 345
<212> TYPE: DNA
<213> ORGANISM: Artificial sequence
<220> FEATURE:
<223> OTHER INFORMATION: Synthetic oligonucleotide, Antibody G2 heavy
      chain variable region

<400> SEQUENCE: 27
```

```
gaggtccagc tgcagcagtc tggacctgag ctggtaaagc ctggggcttc agtgaagatg     60
tcctgcaagg cttctggata cacattcact agctctgtta tgcactgggt gaagcagaag    120
cctgggcagg ccttgagtg gattggatat attaatcctt acaatgatgg tactaagtac    180
aatgagaagt tcaaaggcaa ggccacactg acttcagaca atcctccag cacagcctac    240 atggaactca gcagcctgac ctctgaggac tctgcggtct attactgtgc aaaggggggt    300
aacgatggct actggggcca aggcactact ctcacagtct cctca                    345

<210> SEQ ID NO 28
<211> LENGTH: 324
<212> TYPE: DNA
<213> ORGANISM: Artificial sequence
<220> FEATURE:
<223> OTHER INFORMATION: Synthetic oligonucleotide, Antibody G2 light
      chain variable region

<400> SEQUENCE: 28
gaaattgtgc tcacccagtc tccaaccacc atggctgcat ctcccgggga agatcact      60 atcacctgta gtgccagctc aagtataagt tccatttact tgcattggta tcagcagaag    120
ccaggattct cccctaaagt cttgatttat agggcatcca atctggcttc tggagtccca    180
gctcgcttca gtggcagtgg gtctgggacc tcttactctc tcacaattgg caccatggag    240
gctgaagatg ttgccactta ctactgccag cagggtagta ctataccatt cacgttcggc    300
tcggggacaa agttggaaat aaaa                                           324

<210> SEQ ID NO 29
<211> LENGTH: 216
<212> TYPE: PRT
<213> ORGANISM: Artificial sequence
<220> FEATURE:
<223> OTHER INFORMATION: Synthetic polypeptide, Antibody G2 heavy chain

<400> SEQUENCE: 29

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Asn Asp Gly Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190
```

```
Glu Thr Val Thr Cys Asn Val Ala His Pro Ala Ser Ser Thr Lys Val
        195                 200                 205

Asp Lys Lys Ile Val Pro Arg Asp
    210                 215

<210> SEQ ID NO 30
<211> LENGTH: 215
<212> TYPE: PRT
<213> ORGANISM: Artificial sequence
<220> FEATURE:
<223> OTHER INFORMATION: Synthetic polypeptide, Antibody G2 light chain

<400> SEQUENCE: 30

Glu Ile Val Leu Thr Gln Ser Pro Thr Thr Met Ala Ala Ser Pro Gly
1               5                  10                  15

Glu Lys Ile Thr Ile Thr Cys Ser Ala Ser Ser Ser Ile Ser Ser Ile
            20                  25                  30

Tyr Leu His Trp Tyr Gln Gln Lys Pro Gly Phe Ser Pro Lys Val Leu
        35                  40                  45

Ile Tyr Arg Ala Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Arg Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 31
<211> LENGTH: 648
<212> TYPE: DNA
<213> ORGANISM: Artificial sequence
<220> FEATURE:
<223> OTHER INFORMATION: Synthetic oligonucleotide, Antibody G2 heavy
      chain

<400> SEQUENCE: 31
gaggtccagc tgcagcagtc tggacctgag ctggtaaagc ctggggcttc agtgaagatg      60
tcctgcaagg cttctggata cacattcact agctctgtta tgcactgggt gaagcagaag     120
cctgggcagg gccttgagtg gattggatat attaatcctt acaatgatgg tactaagtac     180
aatgagaagt tcaaaggcaa ggccacactg acttcagaca atcctccag cacagcctac      240 atggaactca gcagcctgac ctctgaggac tctgcggtct attactgtgc aaaagggggt     300
```

-continued

| | | | |
|---|---|---|---|
| aacgatggct | actggggcca | aggcactact | ctcacagtct  cctcagccaa  aacgacaccc | 360 |
| ccatctgtct | atccactggc | ccctggatct | gctgcccaaa  ctaactccat  ggtgaccctg | 420 |
| ggatgcctgg | tcaagggcta | tttccctgag | ccagtgacag  tgacctggaa  ctctggatcc | 480 |
| ctgtccagcg | gtgtgcacac | cttcccagct | gtcctgcagt  ctgacctcta  cactctgagc | 540 |
| agctcagtga | ctgtcccctc | cagcacctgg | cccagcgaga  ccgtcacctg  caacgttgcc | 600 |
| cacccggcca | gcagcaccaa | ggtggacaag | aaaattgtgc  ccagggat | 648 |

<210> SEQ ID NO 32
<211> LENGTH: 648
<212> TYPE: DNA
<213> ORGANISM: Artificial sequence
<220> FEATURE:
<223> OTHER INFORMATION: Synthetic oligonucleotide, Antibody G2 light
      chain

<400> SEQUENCE: 32

| | | | |
|---|---|---|---|
| gaaattgtgc | tcacccagtc | tccaaccacc | atggctgcat  ctcccgggga  gaagatcact | 60 |
| atcacctgta | gtgccagctc | aagtataagt | tccatttact  tgcattggta  tcagcagaag | 120 |
| ccaggattct | cccctaaagt | cttgatttat | agggcatcca  atctggcttc  tggagtccca | 180 |
| gctcgcttca | gtggcagtgg | gtctgggacc | tcttactctc  tcacaattgg  caccatggag | 240 |
| gctgaagatg | ttgccactta | ctactgccag | caggtagta  ctataccatt  cacgttcggc | 300 |
| tcggggacaa | agttggaaat | aaaacgggct | gatgctgcac  caactgtatc  catcttccca | 360 |
| ccatccagtg | agcagttaac | atctggaggt | gcctcagtcg  tgtgcttctt  gaacaacttc | 420 |
| taccccagag | acatcaatgt | caagtggaag | attgatggca  gtgaacgaca  aaatggtgtc | 480 |
| ctgaacagtt | ggactgatca | ggacagcaaa | gacagcacct  acagcatgag  cagcaccctc | 540 |
| acattgacca | aggacgagta | tgaacgacat | aacagctata  cctgtgaggc  cactcacaag | 600 |
| acatcaactt | cacccatcgt | caagagcttc | aacaggaatg  agtgttaa | 648 |

<210> SEQ ID NO 33
<211> LENGTH: 7
<212> TYPE: PRT
<213> ORGANISM: Artificial sequence
<220> FEATURE:
<223> OTHER INFORMATION: Synthetic polypeptide, Antibody G1 Chothia CDR
      H1

<400> SEQUENCE: 33

Gly Phe Thr Phe Ser Asn Tyr
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic polypeptide, Antibody G1 Kabat CDR
      H1

<400> SEQUENCE: 34

Asn Tyr Trp Ile Ser
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic polypeptide, Antibody G1 Chothia

```
        H2

<400> SEQUENCE: 35

Arg Ser Glu Ser Asp Ala Ser Ala
1               5

<210> SEQ ID NO 36
<211> LENGTH: 10
<212> TYPE: PRT
<213> ORGANISM: Artificial sequence
<220> FEATURE:
<223> OTHER INFORMATION: Synthetic polypeptide, Antibody G2 extended CDR
      H1

<400> SEQUENCE: 36

Gly Tyr Thr Phe Thr Ser Ser Val Met His
1               5                   10

<210> SEQ ID NO 37
<211> LENGTH: 7
<212> TYPE: PRT
<213> ORGANISM: Artificial sequence
<220> FEATURE:
<223> OTHER INFORMATION: Synthetic polypeptide, Antibody G2 Chothia CDR
      H1

<400> SEQUENCE: 37

Gly Tyr Thr Phe Thr Ser Ser
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic polypeptide, Antibody G2 Chothia CDR
      H2

<400> SEQUENCE: 38

Asn Pro Tyr Asn Asp Gly
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 39

Gly Ser Lys Ala Phe
1               5
```